(12) United States Patent
Stalker et al.

(10) Patent No.: US 11,376,399 B2
(45) Date of Patent: Jul. 5, 2022

(54) INVENTORY SPARING CATHETER SYSTEM

(71) Applicant: BIOSENSORS INTERNATIONAL GROUP, LTD., Hamilton (BM)

(72) Inventors: Kent C. B. Stalker, San Marcos, CA (US); John D. Whitfield, Temecula, CA (US); Mark C. Bates, Encinitas, CA (US); Peter J. D'Aquanni, Murrieta, CA (US); Jason Andrew Habeger, Carlsbad, CA (US)

(73) Assignee: BIOSENSORS INTERNATIONAL GROUP, LTD., Hamilton (BM)

( * ) Notice: Subject to any disclaimer, the term of this patent is extended or adjusted under 35 U.S.C. 154(b) by 46 days.

(21) Appl. No.: 15/803,402

(22) Filed: Nov. 3, 2017

(65) Prior Publication Data
US 2018/0243533 A1    Aug. 30, 2018

Related U.S. Application Data

(63) Continuation of application No. 12/578,473, filed on Oct. 13, 2009, now abandoned.
(Continued)

(51) Int. Cl.
*A61M 25/01* (2006.01)
*A61M 25/00* (2006.01)
(Continued)

(52) U.S. Cl.
CPC ........ *A61M 25/01* (2013.01); *A61M 25/0041* (2013.01); *A61M 25/10* (2013.01);
(Continued)

(58) Field of Classification Search
CPC .... A61M 25/00; A61M 25/004; A61M 25/10; A61M 25/104; A61M 2205/018;
(Continued)

(56) References Cited

U.S. PATENT DOCUMENTS

| | | |
|---|---|---|
| 3,262,449 A | 7/1966 | Pannier, Jr. et al. |
| 4,033,331 A | 7/1977 | Guss et al. |

(Continued)

FOREIGN PATENT DOCUMENTS

| | | |
|---|---|---|
| JP | H06-023057 | 2/1994 |
| JP | H06-507811 | 9/1994 |

(Continued)

OTHER PUBLICATIONS

International Search Report dated Mar. 29, 2010 in Application No. PCT/US2009/060259.
(Continued)

*Primary Examiner* — Bhisma Mehta
*Assistant Examiner* — Nidah Hussain
(74) *Attorney, Agent, or Firm* — Knobbe, Martens, Olson & Bear LLP

(57) ABSTRACT

Some embodiments relate to a catheter system having a changeable or adjustable working length. The catheter system can comprise a proximal end, a distal end, and a first axial lumen configured to receive a guidewire formed through at least a portion of the catheter body. A first opening can be formed through a portion of the catheter body and be in communication with the first lumen. The sheath can be rotatable, axially movable, or otherwise changeable from at least a first position to a second position, wherein the sheath can substantially cover the first opening in the catheter body in the first position, and can substantially expose the first opening in the catheter body in the second position.

21 Claims, 20 Drawing Sheets

Related U.S. Application Data

(60) Provisional application No. 61/104,678, filed on Oct. 10, 2008.

(51) Int. Cl.
*A61M 25/10* (2013.01)
*A61F 2/958* (2013.01)
*A61M 25/06* (2006.01)

(52) U.S. Cl.
CPC .......... *A61M 25/104* (2013.01); *A61F 2/958* (2013.01); *A61M 2025/0008* (2013.01); *A61M 2025/0063* (2013.01); *A61M 2025/0175* (2013.01); *A61M 2025/0183* (2013.01); *A61M 2025/0681* (2013.01); *A61M 2025/107* (2013.01)

(58) Field of Classification Search
CPC ...... A61M 2025/0183; A61M 25/0013; A61M 25/0015; A61M 25/0041; A61M 25/0051; A61M 25/04; A61M 25/0152; A61M 25/0102; A61M 25/0074; A61M 2025/0062; A61M 2025/0063
USPC ........................................................ 604/524
See application file for complete search history.

(56) References Cited

U.S. PATENT DOCUMENTS

| | | |
|---|---|---|
| 4,738,667 A | 4/1988 | Galloway |
| 4,769,005 A | 9/1988 | Ginsburg et al. |
| 4,771,777 A | 9/1988 | Horzewski et al. |
| 4,773,431 A | 9/1988 | Lodomirski |
| 4,932,413 A | 6/1990 | Shockey et al. |
| 4,988,356 A | 1/1991 | Crittenden et al. |
| 5,135,535 A | 8/1992 | Kramer |
| 5,183,470 A | 2/1993 | Wettermann |
| 5,364,376 A | 11/1994 | Horzewski et al. |
| 5,387,226 A | 2/1995 | Miraki |
| 5,489,271 A | 2/1996 | Andersen |
| 5,545,138 A | 8/1996 | Fugoso et al. |
| 5,591,194 A | 1/1997 | Berthiaume |
| 5,624,396 A | 4/1997 | McNamara et al. |
| 5,688,237 A | 11/1997 | Rozga et al. |
| 5,876,374 A | 3/1999 | Alba et al. |
| 6,143,016 A | 11/2000 | Bleam et al. |
| 6,579,279 B1 | 6/2003 | Rabiner et al. |
| 6,582,459 B1 | 6/2003 | Lau et al. |
| 6,702,781 B1 | 3/2004 | Reifart et al. |
| 7,074,231 B2 * | 7/2006 | Jang ................ A61M 25/104 604/160 |
| 7,402,151 B2 | 7/2008 | Rosenman et al. |
| 7,938,820 B2 | 5/2011 | Webster et al. |
| 8,012,127 B2 | 9/2011 | Lieberman et al. |
| 8,444,625 B2 | 5/2013 | Stalker et al. |
| 10,549,069 B2 | 2/2020 | Boutillette et al. |
| 2003/0088153 A1 | 5/2003 | Carrillo, Jr. et al. |
| 2003/0100886 A1 | 5/2003 | Segal et al. |
| 2003/0199960 A1 | 10/2003 | Paskar |
| 2004/0093056 A1 | 5/2004 | Johnson et al. |
| 2004/0176793 A1 | 9/2004 | Kramer |
| 2006/0032508 A1 | 2/2006 | Simpson |
| 2007/0208302 A1 * | 9/2007 | Webster ................ A61F 2/95 604/103.04 |
| 2007/0282302 A1 | 12/2007 | Wachsman et al. |
| 2008/0097394 A1 | 4/2008 | Lampropoulos et al. |
| 2008/0167628 A1 * | 7/2008 | Li ........................ A61F 2/95 604/264 |
| 2008/0172064 A1 * | 7/2008 | Osborne .......... A61M 25/0662 606/108 |
| 2008/0188804 A1 | 8/2008 | Jordan et al. |
| 2010/0094257 A1 | 4/2010 | Stalker et al. |
| 2010/0222766 A1 | 9/2010 | Stalker et al. |
| 2013/0158396 A1 * | 6/2013 | Vidovich .......... A61M 25/0041 600/434 |

FOREIGN PATENT DOCUMENTS

| | | |
|---|---|---|
| JP | H11-070170 | 3/1999 |
| JP | 2002-126089 | 5/2012 |

OTHER PUBLICATIONS

Office Action dated Sep. 24, 2014 issued U.S. Appl. No. 12/778,985, filed May 12, 2010 in 17 pages.

PCT Partial Search Report for PCT/US2009/060259 dated Feb. 5, 2010 in 11 pages.

PCT Preliminary Report on Patentability and Written Opinion re PCT/US2009/060259, in 34 pages (dated Apr. 12, 2011).

* cited by examiner

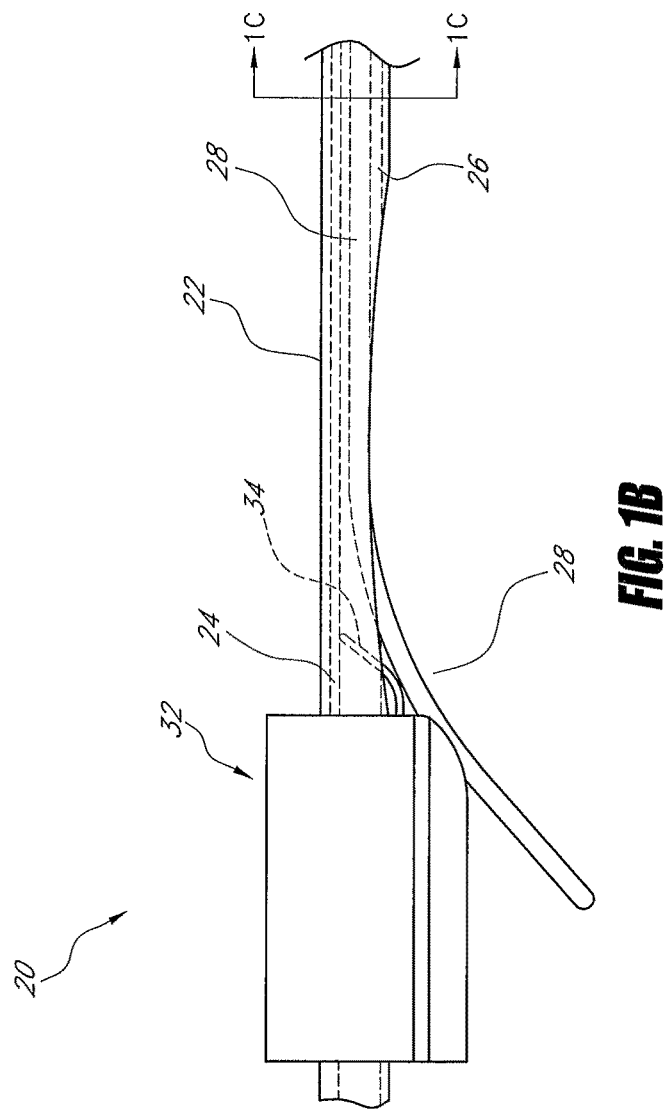

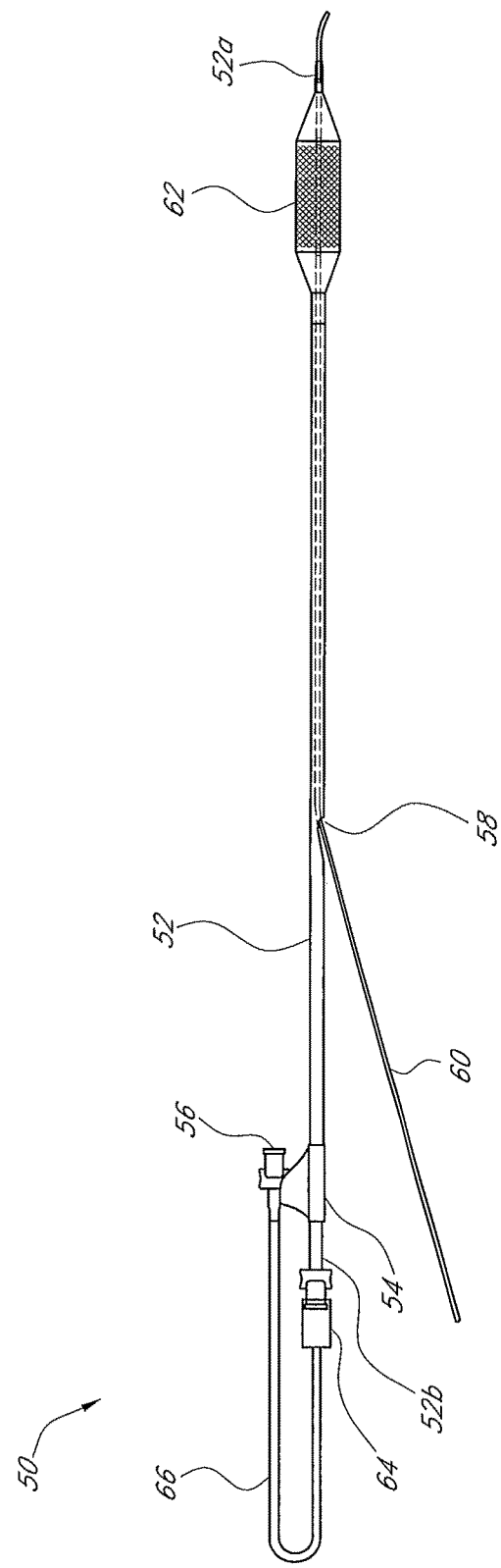
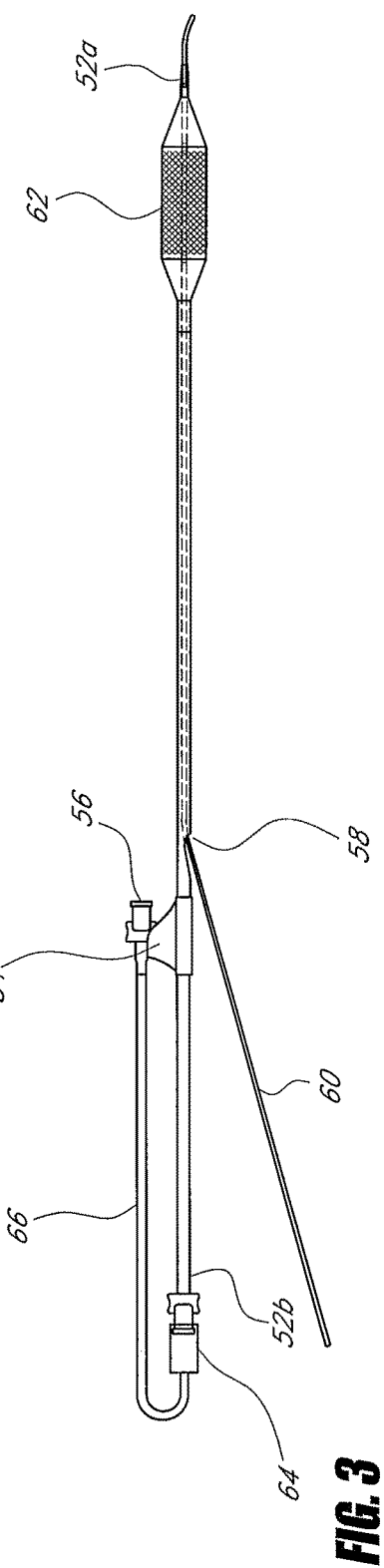

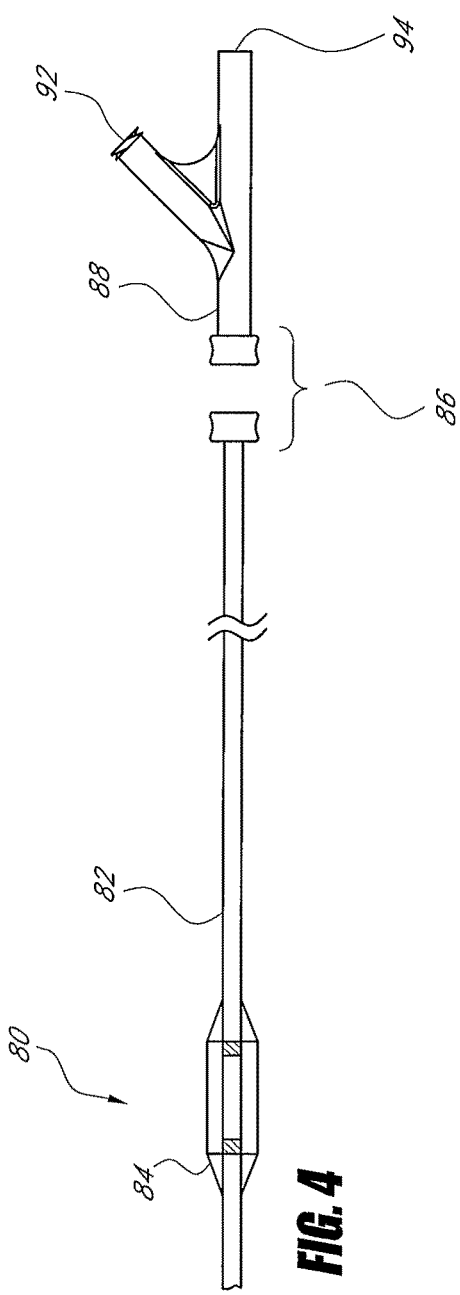
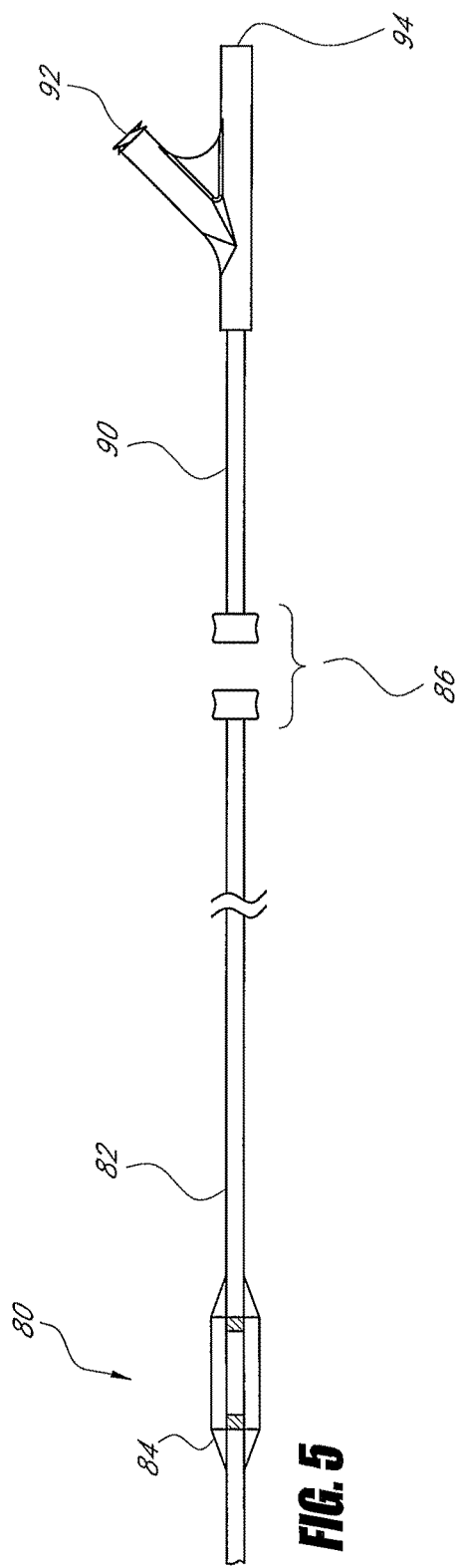

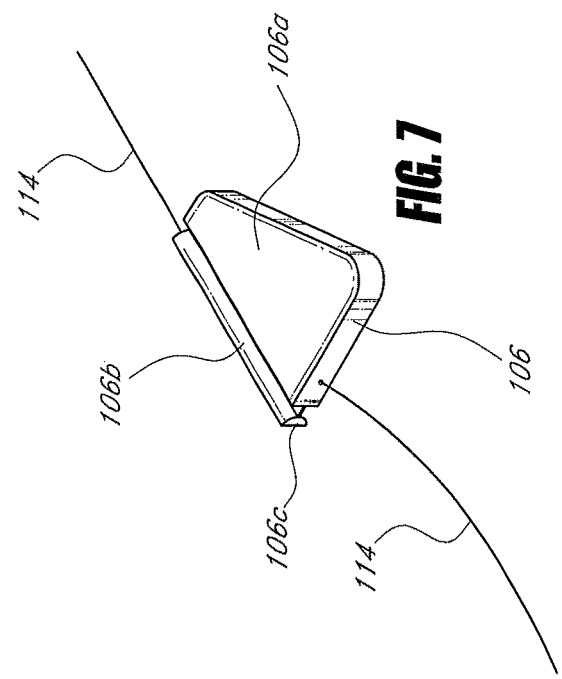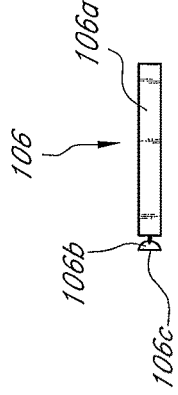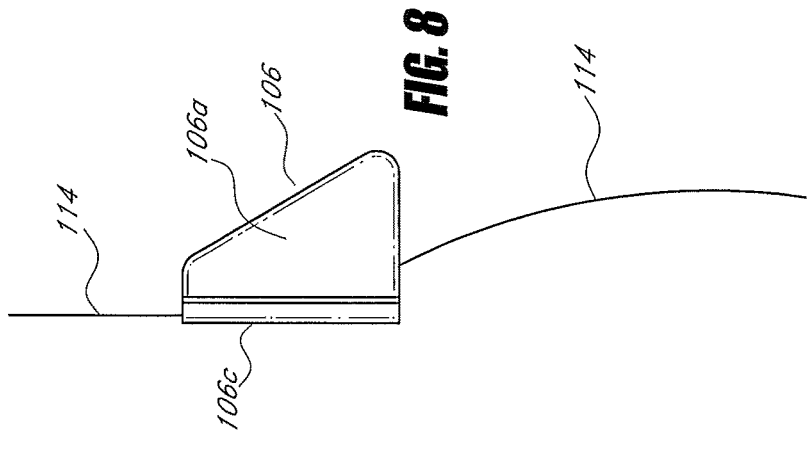

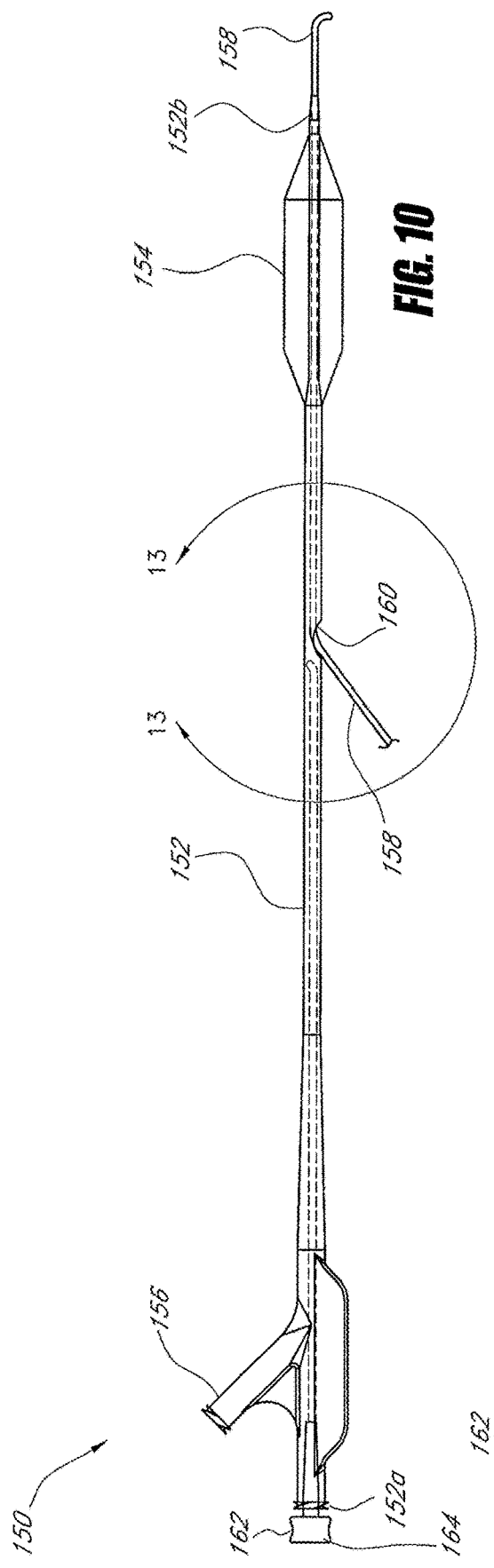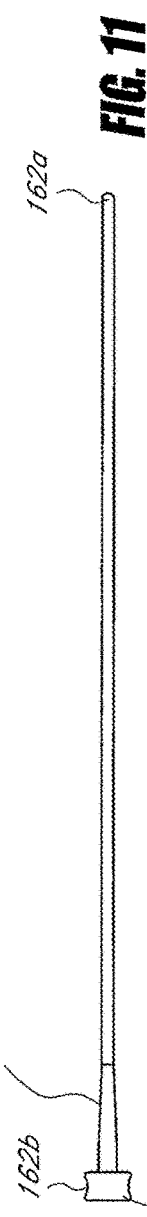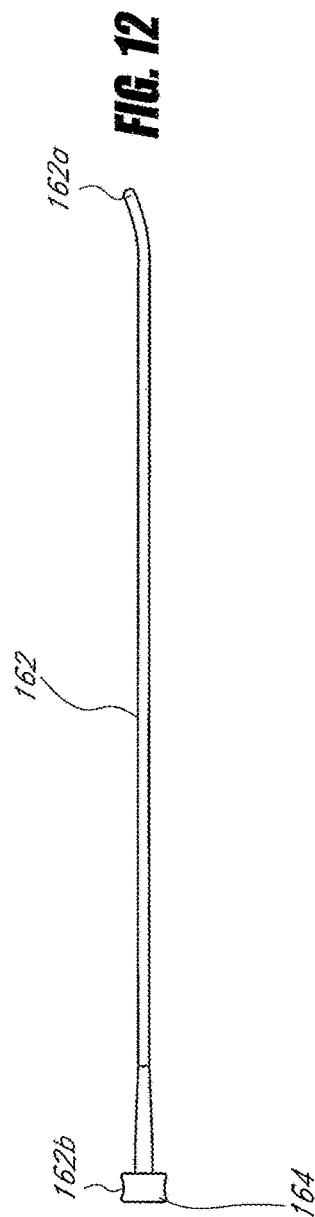

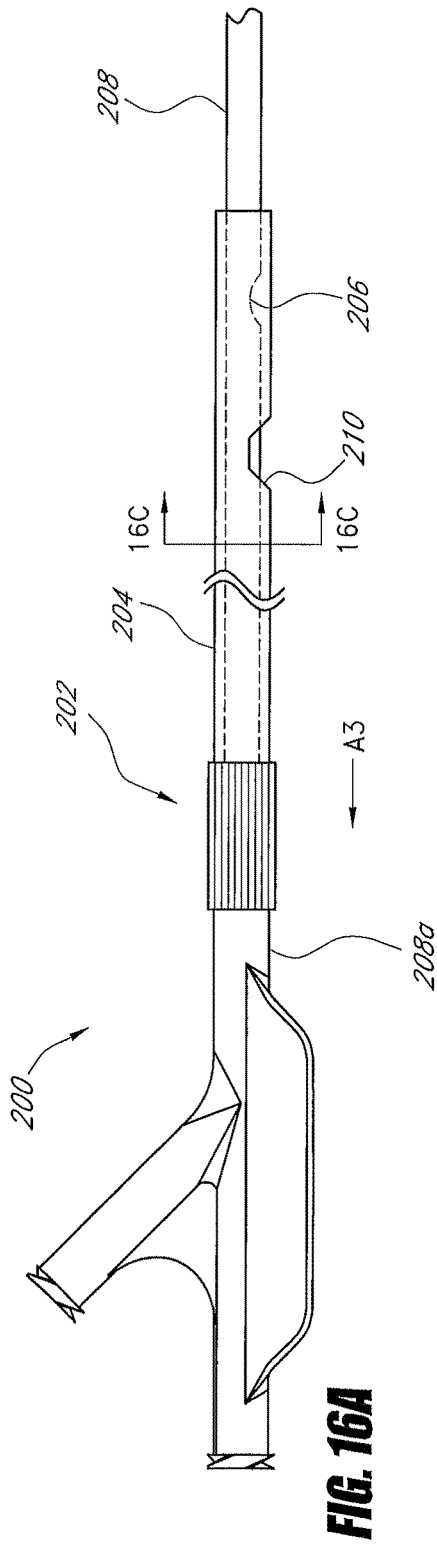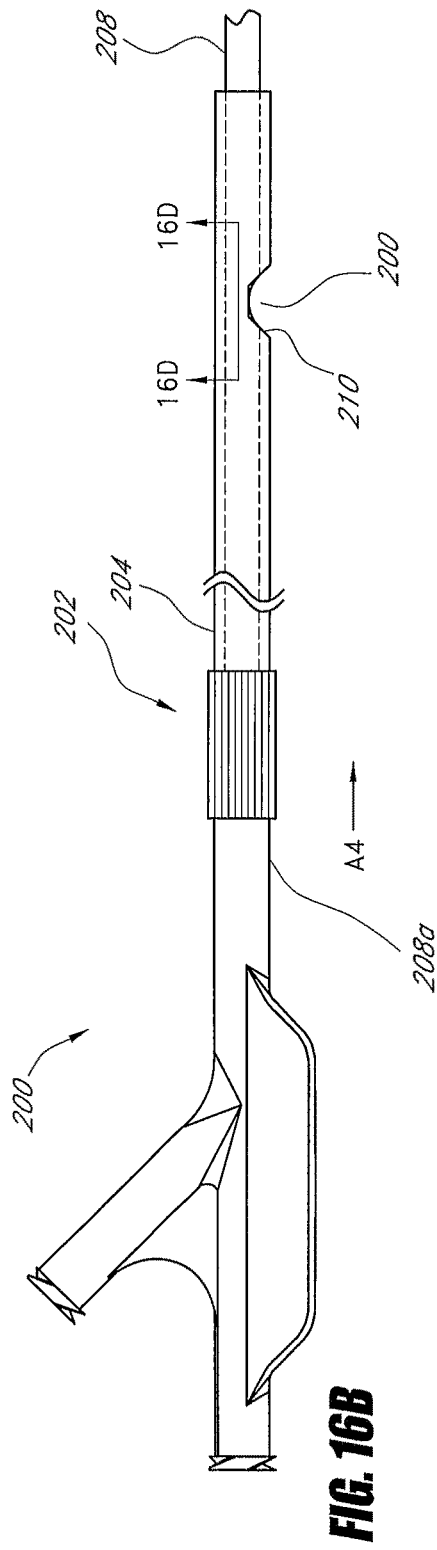

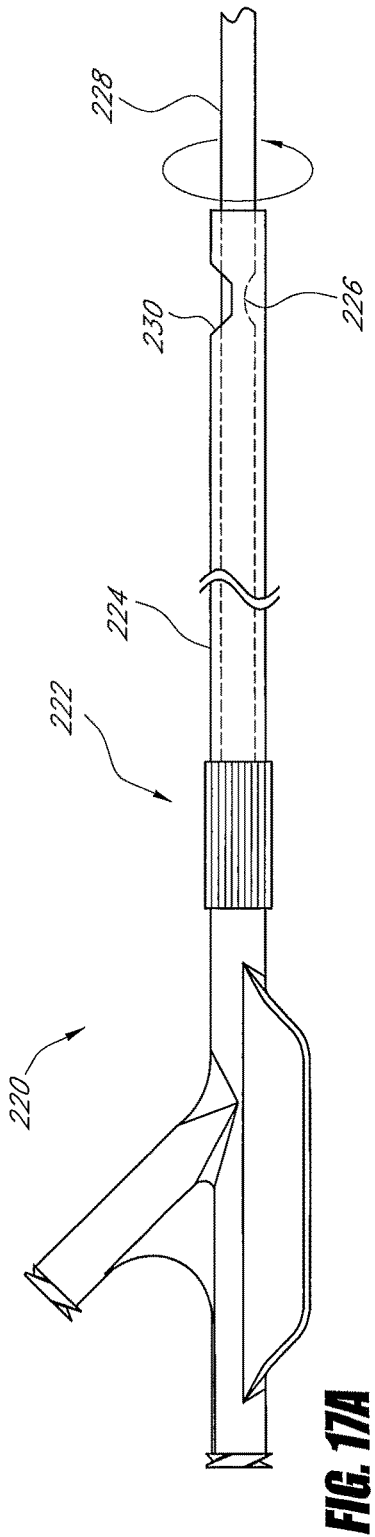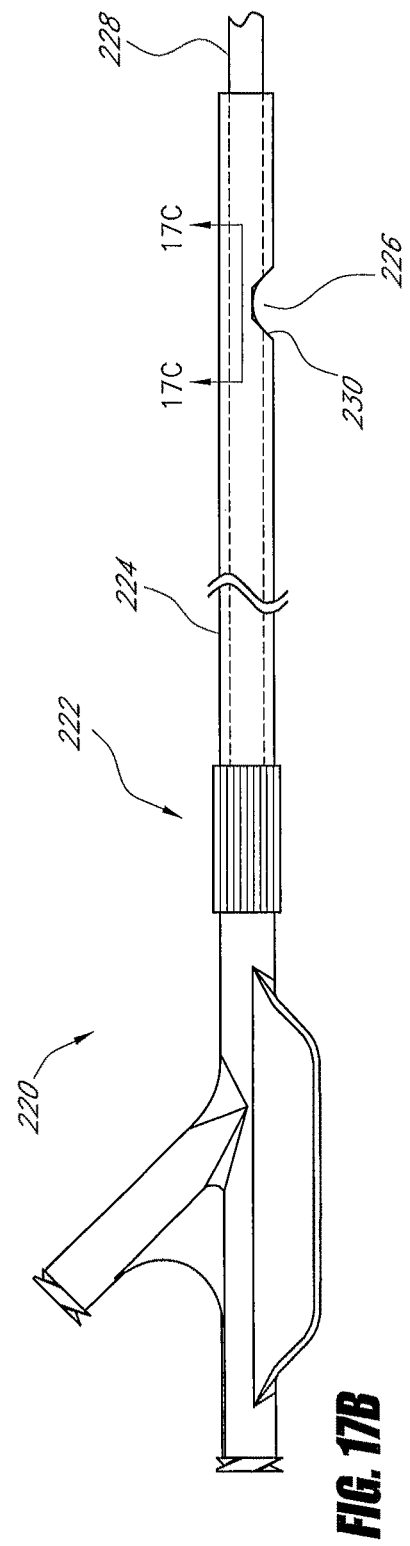

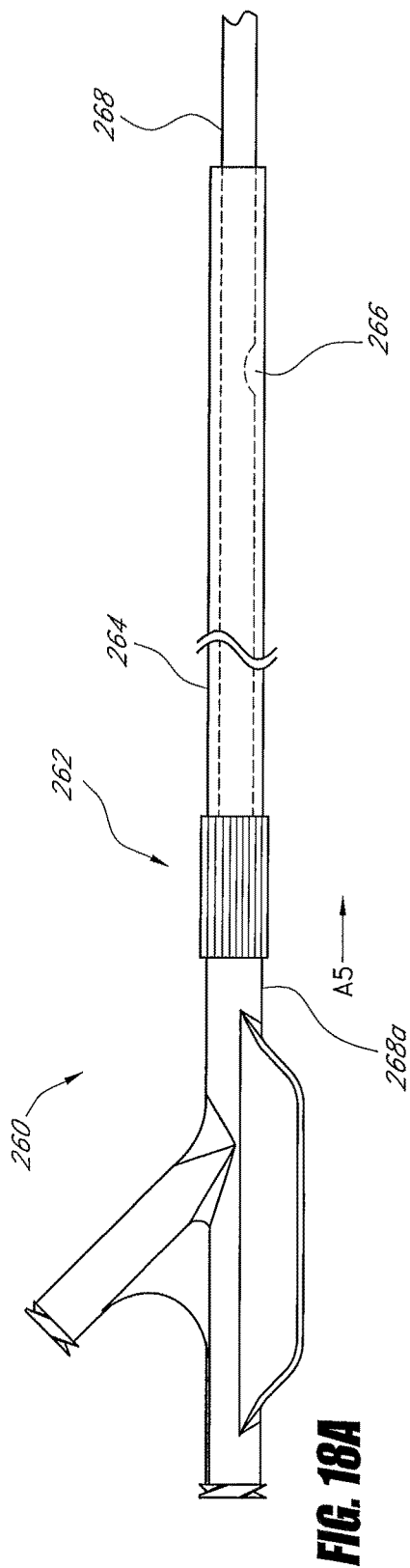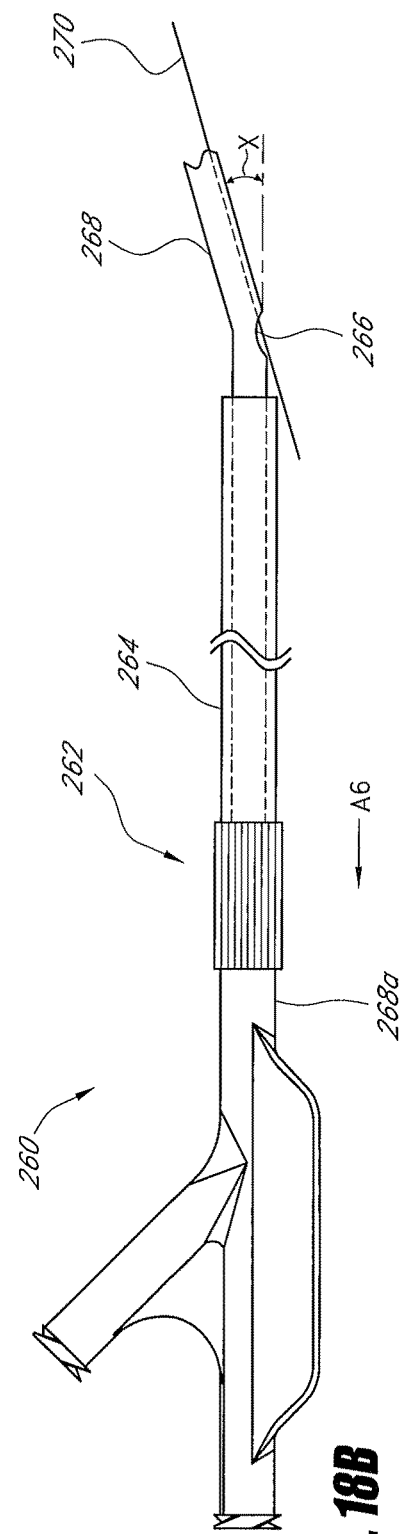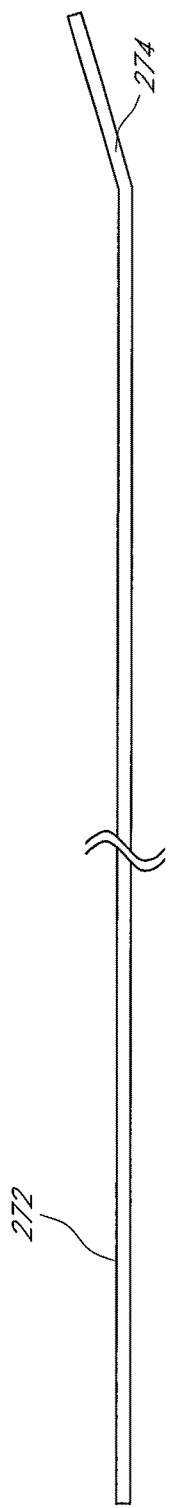

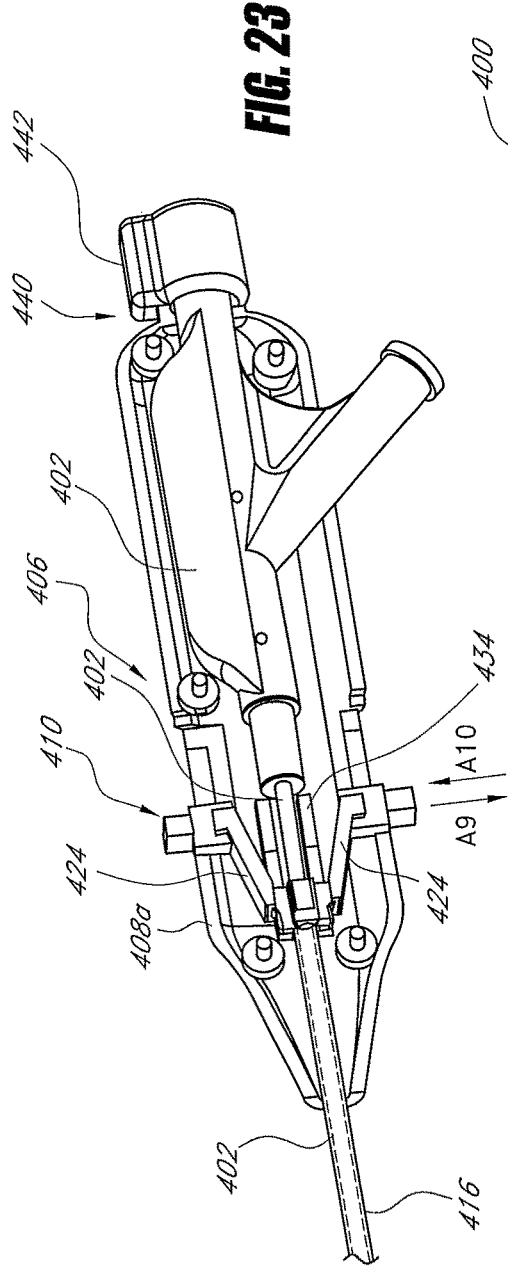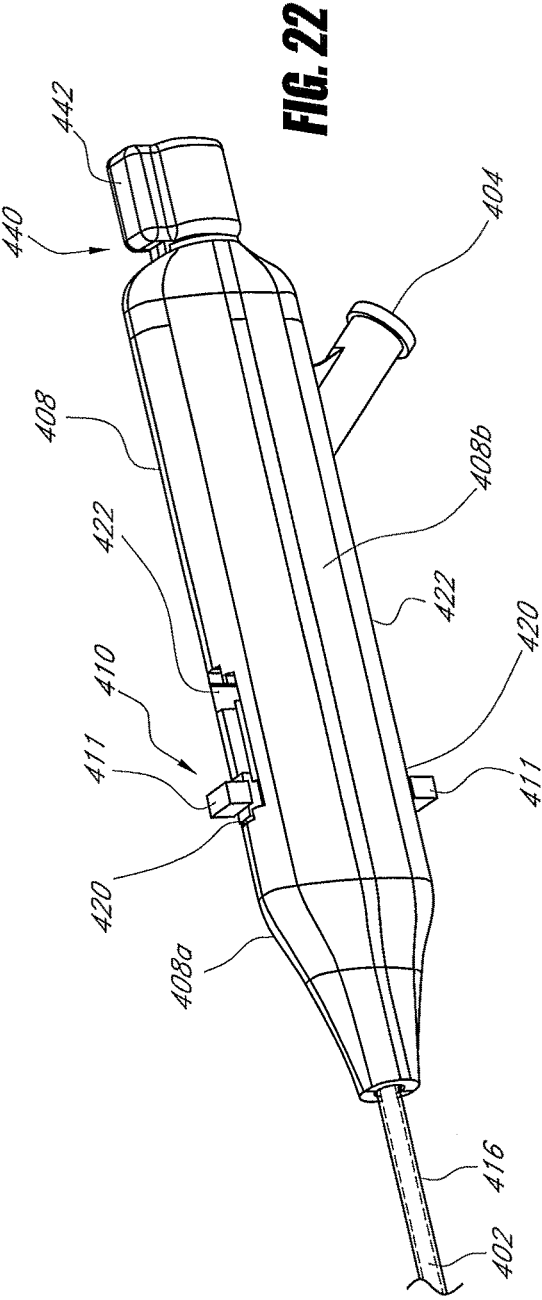

INVENTORY SPARING CATHETER SYSTEM

CROSS-REFERENCE TO RELATED APPLICATION

This application claims the benefit of U.S. application Ser. No. 12/578,473, filed Oct. 13, 2009, which claims priority to U.S. Provisional Application No. 61/104,678, filed Oct. 10, 2008, the entire contents of which are hereby incorporated by reference as if fully set forth herein.

BACKGROUND OF THE DISCLOSURE

Field of the Invention

The present disclosure relates to percutaneous catheters, more particularly, to percutaneous catheters having a changeable working length.

Description of the Related Art

One of the differences with the use of peripheral percutaneous transluminal angioplasty (PTA) catheters compared to percutaneous transluminal coronary angioplasty catheters (PTCA) is the ubiquitous need for different working lengths for PTA catheters. Coronary catheters are designed to traverse a fixed distance between the access point (common femoral, brachial or radial artery) and the heart (or sometimes the brain) to treat lesions. Thus, a single standard PTCA catheter length of 135 cm satisfies almost all the distances needed to treat these lesions irrespective of the patient height and habitus, while at the same time not having too much redundant catheter outside the body. In difference, the target lesions for PTA vary in location and distance from the access site so a single catheter length, if too short, will not reach all the lesions and, if too long, will leave a long unwieldy segment outside the body that is difficult to keep in the sterile field.

For example, PTA catheters may be used to treat lesions very close to the access site with an ispsilateral iliac approach where the distance from the sheath in the common femoral artery to the lesion may be only 5 to 20 cm. Compare this to the patients with lesions in the great vessels like the subclavian artery where the target treatment sites are frequently over 100 cm remote from the femoral access site.

A problem arises when using too long of a catheter in the short distances because the length requires guide wires two times the catheter length, and these often extend below the patient's feet while on the interventional table, and the devices become clumsier and can take two people to load and unload the catheter on the wire. This also creates an increased risk for catheter contamination as the proximal end of the catheter can flip up and hit an unsterile monitor or even reach the floor. In these instances the entire system must be discarded and the procedure begins all over again. Hence, there is a preference for shorter catheters when the target lesion is close to the access site, and for longer catheters when treating more distal lesions that cannot be reached by shorter catheters. Shorter catheters are simpler in the close proximity cases and require less labor and time under fluoroscopy (i.e. radiation exposure).

This need for different length catheters creates a burden on the end user in the hospital catheter lab to stock large amounts of inventory due to all the combinations of lengths and sizes. Catheters may be chosen by guide wire size (e.g., 0.014", 0.018", or 0.035"), balloon pressures/compliance (i.e. high pressure non-compliant, or low pressure compliant), over a range of balloon diameters and balloon lengths, and by whether the systems are balloon only or balloons with stents mounted on them. In the domain of PTA, the inventory is doubled by the need for 2 or more working lengths. This leads to thousands of units being stocked and accounted for in the hospital catheter lab, for example up to 3 wire sizes×2 pressure types×10 diameters×8 balloon lengths×2 catheter lengths, plus having multiples of each size available. Layered on top of this, the catheterization laboratory may need multiple product types from multiple suppliers since different products are needed for different lesions.

Recent changes in Joint Commission on the Accreditation of Healthcare Organizations (JCAHO) guidelines make it more difficult for hospitals to maintain inventory and protect products from contamination. Many hospitals have shifted to closed inventory management systems with limited space. In a typical hospital, about 60 percent of the total supply cost is driven by three clinical service areas: surgery, cardiology and pharmacy (source: 2004 VHA Supply Cost Benchmarking Database; VHA, Inc.). Forty percent of supply costs can be attributed to implants, stents, and other devices (source: Serb, Chris; Strategic Savings; Hospitalconnect.com; Apr. 16, 2004). Add to this that many hospitals are pushing companies to provide products on consignment, then additional costs are also funneled back to the companies that manufacture the product.

SUMMARY OF SOME EXEMPLIFYING EMBODIMENTS

Some embodiments of this disclosure relate to a catheter system having a catheter body comprising a proximal end, a distal end, and a first lumen formed through at least a portion of the catheter body. The first lumen can be configured to receive a guidewire. In some embodiments, a first opening can be formed through at least a portion of the catheter body. The first opening can be in communication with the first lumen. In some embodiments, the catheter system can have a sheath (also referred to herein as an outer sheath) supported by the catheter body, the sheath having a second opening formed through an outer wall of the sheath. The sheath can be configured to be movable between at least a first position and a second position. In some embodiments, in the second position, at least a portion of the second opening of the sheath is approximately aligned with the first opening of the catheter body, and, in the first position, no portion of the second opening of the sheath is aligned with the first opening of the catheter body.

Some embodiments of this disclosure relate to a catheter system comprising a catheter body having a proximal end, a distal end, and a first lumen formed through at least a portion of the catheter body, the first lumen being configured to receive a guidewire. A first opening can be formed through at least a portion of the catheter body, the first opening being in communication with the first lumen. Additionally, a sheath can be supported by the catheter body. The sheath can have a second opening formed through an outer wall of the sheath. In some embodiments, the sheath can be movable between at least a first position and a second position. The catheter system can be configured such that at least a portion of the second opening of the sheath is adjacent to the first opening of the catheter body when the sheath is in the first position and such that no portion of the second opening of the sheath is adjacent to the first opening of the catheter body when the sheath is in the second position.

Some embodiments of this disclosure relate to a catheter system comprising a catheter body having a proximal end, a distal end, and a first lumen formed axially through at least a portion of the catheter body, the first lumen being configured to receive a guidewire. The catheter system can have a first opening formed through at least a portion of the catheter body, the first opening being in communication with the first lumen. The catheter body can be biased to be angled at an acute angle adjacent to the first opening when the catheter body is in a relaxed configuration.

Some embodiments of this disclosure relate to a catheter system comprising a catheter body having a proximal end, a distal end, and a first lumen formed through at least a portion of the catheter body. The first lumen can be configured to receive a guidewire. A diverter can be positioned at any of a plurality of positions along the length of the catheter body. In some embodiments, the catheter body can be substantially sealed along the length thereof such that the first lumen is substantially sealed along the length thereof. The diverter can be configured such that at least a portion of the diverter passes through the catheter body such that an opening formed in the diverter communicates with the first lumen, whereby a guidewire that is advanced through the first lumen can be advanced through the opening formed in the diverter.

Some embodiments of this disclosure relate to a catheter system comprising a catheter body having a proximal end, a distal end, and a first lumen formed axially through at least a portion of the catheter body, the first lumen being configured to receive a guidewire. A first opening can be formed through at least a portion of the catheter body, the first opening being in communication with the first lumen. The catheter system can also have a sheath supported by the catheter body, the sheath being slidable relative to the catheter body. The sheath can be movable between at least a first position and a second position. In the first position, the first opening can be substantially covered by the sheath. In the second position, the first opening can be substantially uncovered. Further, when the sheath is in the second position, the catheter system can be configured to direct a guidewire being advanced through the first lumen to pass through the first opening. In some embodiments, the catheter body can define an inflection point adjacent to the first opening, the inflection point being the approximate point wherein the catheter body defines a bend, a curve, an angle, or other suitable change in the orientation of the catheter body. The catheter body can be movable between at least a first configuration and a second configuration, wherein an angle at the inflection point is greater in the first configuration than in the second configuration. In some embodiments, the bend of the catheter body in the first configuration can comprise a first inwardly bent portion and a second outwardly bent portion that is circumferentially opposite the first inwardly bent portion, the first inwardly bent portion defining a first interior angle between the proximal catheter body portion and the distal catheter body portion. The second outwardly bent portion can define a second exterior angle between the proximal catheter body portion and the distal catheter body portion. The second exterior angle can be greater than the first interior angle in the first configuration. The first opening can be positioned along the second outwardly bent portion such that the catheter body is bent away from the first opening in the first configuration, the first opening positioned relative to the inflection point such that, in the first configuration, the guidewire can pass through the first lumen from the distal portion of the catheter body within the body of the patient, out of the first lumen through the first opening and in a proximal direction outside the body of the patient.

Some embodiments of this disclosure relate to a catheter system comprising a catheter body having a proximal end, a distal end, and a first lumen formed axially through at least a portion of the catheter body, the first lumen being configured to receive a guidewire. A first opening can be formed through at least a portion of the catheter body, the first opening being in communication with the first lumen. The catheter system can further comprise a sheath supported by the catheter body, the sheath having a second opening formed through an outer wall thereof. In some embodiments, the sheath can be movable between at least a first position and a second position such that, in the second position, at least a portion of the second opening of the sheath can be approximately aligned with the first opening of the catheter body, and, in the first position, no portion of the second opening of the sheath is aligned with the first opening of the catheter body.

Some embodiments of this disclosure relate to a catheter system comprising a catheter body having a proximal end, a distal end, and a first lumen formed axially through at least a portion of the catheter body, the first lumen being configured to receive a guidewire, and a first opening formed through at least a portion of the catheter body, the first opening being in communication with the first lumen. In some embodiments, the catheter body can define an inflection point adjacent to the first opening, the inflection point being the approximate location wherein the catheter body defines a bend having an angle. Further, the catheter body can be movable between at least a first configuration and a second configuration, and the angle can be greater in the first configuration than in the second configuration.

Some embodiments of this disclosure relate to a catheter system comprising a catheter body comprising a proximal end, a distal end, and a first lumen axially formed through at least a portion of the catheter body, the first lumen being configured to receive a guidewire, and a diverter that can be positioned at any of a plurality of positions along the length of the catheter body. In some embodiments, the diverter can be configured such that at least a portion of the diverter passes through the catheter body into the first lumen such that an opening formed in the diverter communicates with the first lumen, whereby a guidewire that can be advanced through the first lumen can be advanced through the opening formed in the diverter.

Some embodiments of this disclosure relate to a method of using a catheter, comprising advancing a catheter body over a guidewire positioned within a bodily vessel so that the guidewire passes at least partially through a first lumen formed axially through at least a portion of the catheter body and through a first opening of the catheter body, moving a sheath positioned about the catheter body from a first position to a second position, and diverting the guidewire so that, when the sheath is in the second position, the guidewire passes through the first opening formed in the catheter body as the catheter is advanced over the guidewire. In some embodiments, the sheath can substantially cover the first opening when the sheath is in a first position. In some embodiments, at least a portion of the first opening can be uncovered when the sheath is in the second position.

Some embodiments of this disclosure relate to a method of using a catheter, comprising advancing a distal portion of a catheter body over a guidewire positioned within a bodily vessel so that the guidewire passes through a lumen formed axially in the catheter body, diverting the guidewire through a side-wall opening formed in the catheter body, and advancing the distal portion of the catheter into an introducer sheath positioned in a patient's body to a treatment site while maintaining a proximal portion of the catheter body at least up the side-wall opening proximal of the introducer sheath. The side-wall opening can be in communication with the lumen.

Some embodiments of this disclosure relate to a method of using a catheter, comprising advancing a catheter body into a patient's vasculature, the catheter body comprising a proximal end, a distal end, a first lumen configured to receive a guidewire formed axially through at least a portion of the catheter body, and a bend at an inflection point adjacent to the first opening. The catheter body can be movable between at least a first configuration and a second configuration, and the angle of the bend can be greater in the first configuration than in the second configuration. The method can further comprise moving the catheter body from the first configuration to the second configuration to reduce the angle of the bend, and advancing the catheter body over a guidewire positioned within a bodily vessel so that the guidewire passes through the first lumen and past the first opening of the catheter body.

Some embodiments of this disclosure relate to a method of using a catheter, comprising advancing the catheter over a guidewire positioned within a bodily vessel so that the guidewire passes through a first lumen formed in a catheter body. The method can also comprise moving a sheath positioned about the catheter body from a first position (wherein the sheath can substantially cover a first opening formed in the catheter body) to a second position (wherein at least a portion of the first opening is not covered by the sheath). The first opening formed in the catheter body can be in communication with the first lumen formed in the catheter body. The method can also comprise diverting the guidewire so that, when the sheath is in the second position, the guidewire advances through the first opening formed in the catheter body as the catheter is advanced over the guidewire.

BRIEF DESCRIPTION OF THE DRAWINGS

The foregoing summary, as well as the following detailed description of the preferred embodiments of the present invention, will be better understood when read in conjunction with the appended drawings, in which:

FIG. 1B is a side view of the embodiment of the catheter system illustrated in FIG. 1A.

FIG. 2 is a side view of another embodiment of a catheter system, showing the catheter system in a longer inserted length configuration.

FIG. 3 is a side view of the embodiment of a catheter system shown in FIG. 2, showing the catheter system in a shorter inserted length configuration.

FIG. 4 is a side view of another embodiment of a catheter system, showing the catheter system in a shorter inserted length configuration.

FIG. 5 is a side view of the embodiment of the catheter system shown in FIG. 4, showing the catheter system in a longer inserted length configuration.

FIG. 7 is a perspective view of the embodiment of the slider mechanism shown in FIG. 6.

FIG. 8 is a side view of the embodiment of the slider mechanism shown in FIG. 6.

FIG. 9 is an end view of the embodiment of the slider mechanism shown in FIG. 6.

FIG. 10 is a side view of another embodiment of a catheter system.

FIG. 11 is a top view of an embodiment of the mandrel shown in FIG. 10.

FIG. 12 is a side view of an embodiment of the mandrel shown in FIG. 10.

FIG. 16A is a side view of another embodiment of a catheter system, showing the catheter system in a first configuration.

FIG. 16B is a side view of the embodiment of a catheter system shown in FIG. 16A, showing the catheter system in a second configuration.

FIG. 17A is a side view of another embodiment of a catheter system, showing the catheter system in a first configuration.

FIG. 17B is a side view of the embodiment of a catheter system shown in FIG. 17A, showing the catheter system in a second configuration.

FIG. 18A is a side view of another embodiment of a catheter system, showing the catheter system in an extended configuration.

FIG. 18B is a side view of the embodiment of the catheter system shown in FIG. 18A, showing the catheter system in a shorter inserted length configuration.

FIG. 18C is a side view of an embodiment of a mandrel that can be used with the embodiment of the catheter system shown in FIGS. 18A and 18B.

FIG. 22 is a perspective view of another embodiment of a catheter system.

FIG. 23 is a perspective view of the embodiment of a catheter system shown in FIG. 22, with a portion of the housing removed for clarity.

DETAILED DESCRIPTION OF SOME EXEMPLIFYING EMBODIMENTS

The embodiments of the present disclosure reduce catheter inventory by providing balloon catheter or any other suitable catheter having an adjustable length. Having the capability to adjust the working length of the catheter can reduce the number of inventoried catheters significantly, in some cases in half. Some embodiments can utilize a notch or opening in the catheter shaft or body at a position where it would be advantageous to permit a guidewire to exit. In some embodiments, the notch location can be the same as in a shorter catheter length, in most cases approximately 80-85 cm proximal of the tip of the catheter. The opening can also be located close enough to the proximal end of the catheter such that it does not enter the introducer sheath (or the body). For example, the catheter can be configured such that the opening will be covered if it is to be inserted into the guide catheter or introducer sheath, i.e., if an extended working length is needed for lesion access.

Additionally, with conventional apparatuses, the inflation lumen can be approximately 1-2 feet behind where the physician is standing (near the sheath), causing him/her to have to move back and forth to operate the inflation lumen. To solve this dilemma, as will be described in greater detail, in some embodiments, the catheter can have a movable inflation port that can be movable to accommodate the physician's position.

In some embodiments, a catheter can be provided that can have a catheter body having a guidewire lumen and an inflation lumen axially formed therein. An inflatable balloon can be supported on a distal portion of the catheter body. The catheter can be configured such that the working length (e.g., the length of the catheter to be positioned inside a patient during use) of the catheter body can be increased or decreased depending on the individual patient need.

Figure 1A:
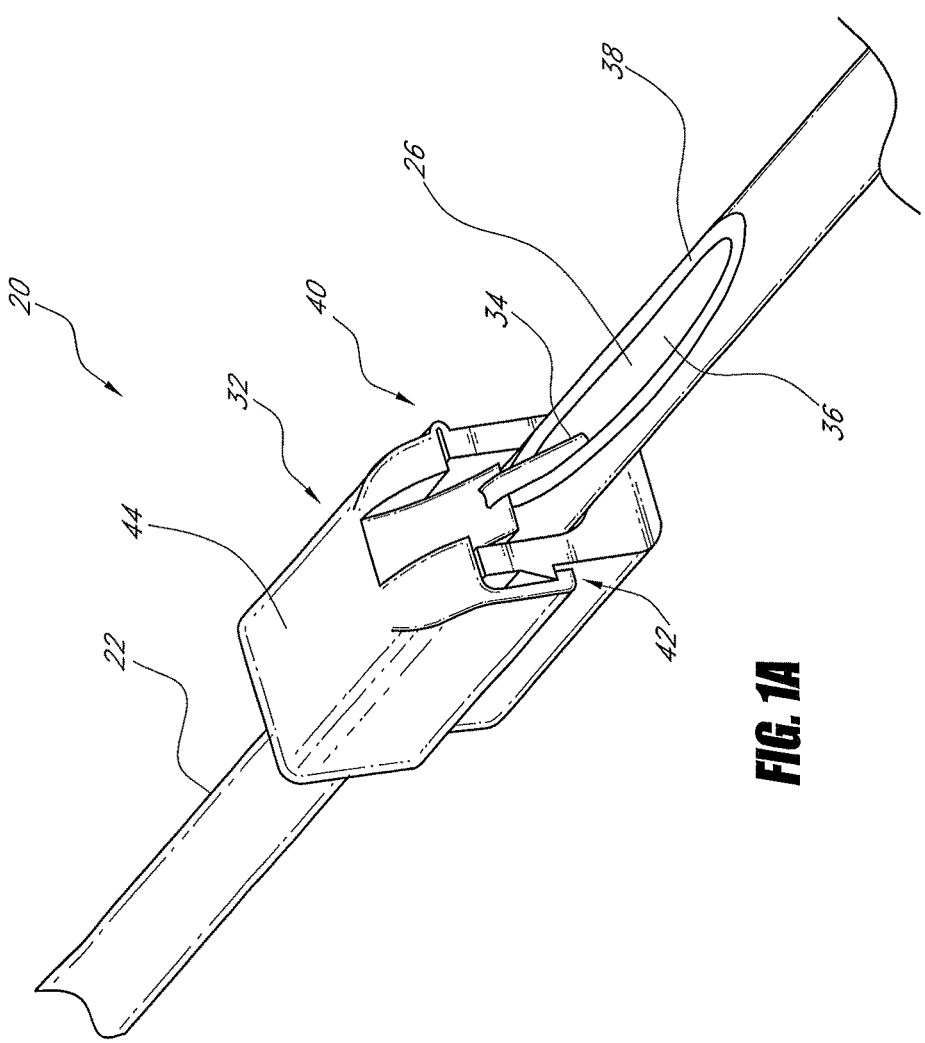
FIG. 1A is a perspective view of an embodiment of a catheter system.
Figure 1C:
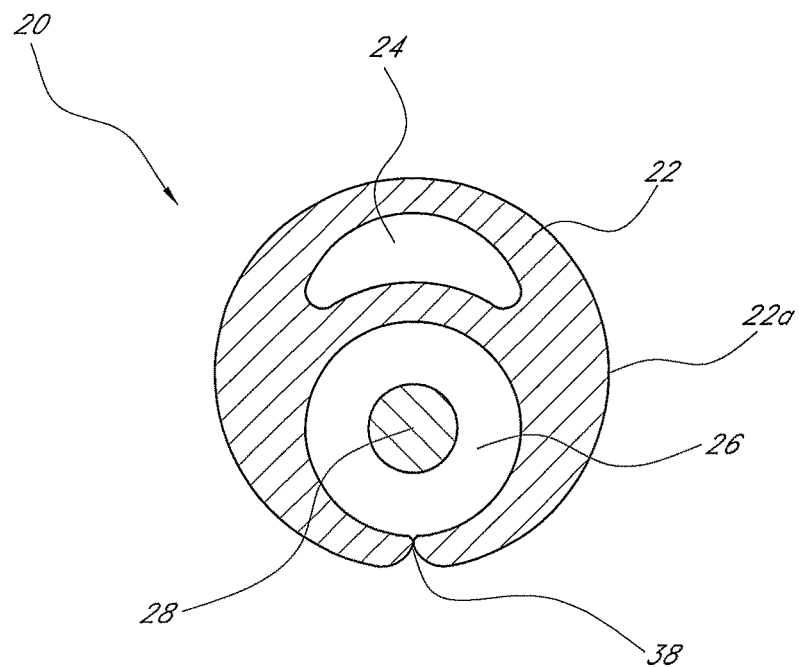
FIG. 1C is a section view of the embodiment of the catheter system shown in FIG. 1A, taken through line 1C-1C in FIG. 1B.

FIG. 1A is a perspective view of an embodiment of a catheter system 20. FIG. 1B is a side view of the embodiment of the catheter system 20 illustrated in FIG. 1A. FIG. 1C is a section view of the embodiment of the catheter system 20 shown in FIG. 1A, taken through line 1C-1C in FIG. 1B. In some embodiments, the catheter system 20 can comprise features, components, configurations, or other details found in conventional catheter systems, in addition or in the alternative to features, components, configurations, or other details described herein.

With reference to FIGS. 1A-1C, the catheter system 20 can comprise a catheter body 22 having an inflation lumen 24 and a guidewire lumen 26. At least a portion of, or the entire length of, the guide wire lumen 26 can be configured to slidingly receive a guidewire 28 (omitted from FIG. 1A for clarity). The guidewire 28 can exit the lumen 26 at the distal end of the catheter body 22 through an opening (not illustrated) in communication with the guidewire lumen 26.

An interface mechanism 32 can be positioned on the catheter body 22 to surround at least a portion of the outside surface of the catheter body 22. In some embodiments, the interface mechanism 32 can be configured to be slidingly positionable along the length of the catheter body 22. The interface mechanism 32 can also be configured to be completely removable from the catheter body 22. For example, the interface mechanism 32 and/or the catheter body 22 can have detents, clamps, or other features to selectively secure the interface mechanism 32 at a desired position along the length of the catheter body 22.

The guidewire lumen 26 can be configured to be at least substantially sealed along a substantial portion of its length other than at the opening accessed by the interface mechanism 32. In some embodiments, the interface mechanism 32 comprises a lever arm or blade 34 that is configured to create an opening or provide access to a preexisting opening in the lumen wall between the guidewire lumen 26 and an outside surface 22a of the catheter body 22. The lever arm or blade 34 can provide a passageway 36 to the guidewire lumen 26 at any of a variety of longitudinal positions on the catheter body 22.

In some embodiments, the lever or blade 34 creates an opening by pressing down on the lumen wall to open a slit 36, as illustrated in FIG. 1C. The blade 34 can also be used to open a portion of a slit created in the lumen wall between the outside surface 22a of the catheter body 22 and the guidewire lumen 26. FIG. 1C depicts a catheter cross-section that comprises a preformed opening or slit 38 allowing access to the guidewire lumen 26 at a multitude of locations along the length of the catheter body 22. In some embodiments, as depicted in FIGS. 1A and 1B, the lever arm or blade 34 is configured to extend into an opening or slit 38 in the lumen wall and to divert the guidewire 28 out of the lumen 26. In some embodiments, the lever or blade 34 extends into the opening or slit 38 to divert the guidewire 28 out of the lumen 26.

In some embodiments, the catheter system 20 can be configured to permit the location of the passageway 36 to be moved as the interface mechanism 32 is moved along the catheter body 22, while sealing the other portions of the catheter body 22 so that the guidewire lumen remains substantially sealed along its length. In some embodiments, the opening or slit 38 can be formed in the catheter body 22 adjacent to the guidewire lumen 26. The opening or slit 38 can be configured so that the blade 34 can create the opening along any desired portion of the catheter body, even with the guidewire 28 occupying the opening 36. The opening or slit 38 can be self-sealing such that it is biased to form a closed seal along the length of the catheter body 22 adjacent to the lumen 26.

The sealed passageway 36 can be configured to receive the guidewire 28 and provide a sealed conduit for the guidewire 28 to the guidewire lumen 26. In this arrangement, the interface mechanism 32 can be moved along the length of the catheter body 22 to provide the adjustment of the position of the opening 36. In this arrangement, the working length of the catheter system 20 can be changed by moving the interface mechanism 32 along the length of the catheter body 22.

In some embodiments, the interface mechanism 32 can define a hinge member 40 and a latching mechanism 42. The hinge member 40 and latching mechanism 42 shown most clearly in FIG. 1A can be configured such that a user can open a cover portion 44 of the interface mechanism 32 so that the interface mechanism 32 can be removed from or assembled with the catheter body 22.

FIG. 2 is a side view of another embodiment of a catheter system 50, showing the catheter system 50 in a longer inserted length configuration. FIG. 3 is a side view of the embodiment of a catheter system 50 shown in FIG. 2, showing the catheter system 50 in a shorter inserted length configuration. In some embodiments, the catheter system 50 can have a catheter body 52, a sliding mount 54, an inflation lumen fitting 56, and a guidewire exchange port 58. An inflation balloon 62 can be supported by the catheter body 52. As illustrated, the sliding mount 54 can be slidably positionable on the catheter body 52 so that the position of the inflation lumen fitting 56 (which can have a luer fitting on the end thereof) can be adjustable. For example, in the longer inserted length configuration shown in FIG. 2, the inflation lumen fitting 56 can be positioned farther away from the guidewire exchange port 58 as compared to the shorter inserted length configuration of the catheter system 50 shown in FIG. 3. In some embodiments, a user can shorten the distance between the inflation lumen fitting 56 by sliding the inflation lumen fitting 56 along the catheter body 52 toward a guidewire exchange port 58 through which a guidewire 60 can pass to enter into or exit from the guidewire lumen formed in the catheter body 52. In some embodiments, the guidewire exchange port 58 can be in a fixed position along the catheter body 52. In some embodiments, the position of the guidewire exchange port 58 can be adjustable.

In some embodiments, the sliding mount 54 can be moved toward the distal end 52a of the catheter body 52 (e.g., closer to the guidewire exchange port 58) to shorten the working portion of the catheter body 52. The shorter inserted length configuration is illustrated in FIG. 3. In this configuration, the user then can work with a shorter catheter and guidewire working length, with the inflation port 56 being close to the guidewire port 58. This innovation enables the physician not to have to move down the operating table to actuate an inflation device coupled with the inflation lumen of the catheter system 50.

In some embodiments, the sliding mount 54 can be pulled back toward the proximal end 52b of the catheter body 52 to lengthen the working length or portion of the catheter body 52. This configuration is illustrated in FIG. 2.

In some embodiments, all or a portion of the catheter body 52 can be stiffened with a stiffening mandrel, braids, wires, coils, a stiff or rigid material, or otherwise to enable the catheter body 52 to be pushed without buckling or inadvertently bending during use of the catheter system 50. In some embodiments, the distance between the location of the guidewire port 58 and a coupling 64 (discussed further below) can be between approximately 40 cm and approximately 80 cm. In some embodiments, the distance between the location of the guidewire port 58 and the distal end of the catheter 52a can be approximately 60 cm or greater.

In the illustrated embodiment, the guidewire 60 can pass through the guidewire lumen and exit the catheter body 52 at the distal end 52a thereof. Additionally, in some embodiments, an inflation balloon 62 can be supported by the catheter body 52 near the distal end 52a of the catheter body 52. As such, the catheter system 50 can be configured for an angioplasty treatment, for stent delivery or other treatment for which a balloon is useful.

In some embodiments, the catheter system 50 can have an inflation lumen coupling 64 that can provide a coupling between the inflation lumen fitting or port 56 and the remaining portion of the catheter body 52. A length of tubing 66 can provide a flexible conduit between the inflation port 56 and the coupling 64.

FIG. 4 is a side view of another embodiment of a catheter system 80, showing the catheter system 80 in a shorter inserted length configuration. FIG. 5 is a side view of the embodiment of the catheter system 80 shown in FIG. 4, showing the catheter system 80 in a longer inserted length configuration. As illustrated in FIGS. 4 and 5, the catheter system 80 can have a catheter body 82, an inflation balloon 84, and a quick connect coupling 86. The catheter body 82 can include an inflation lumen and a guidewire lumen. As illustrated in FIG. 4, the quick connect coupling 86 can be used to connect a short extension 88 to the catheter body 82. The short extension 88 can have an inflation lumen port 92 and an exit port 94 for the guidewire lumen. A long extension 90 shown in FIG. 5 can have an inflation lumen port 92 and an exit port 94 for the guidewire lumen. The catheter system 80 can be configured such that the short extension 88 and the long extension 90 can be interchangeably joined to the quick connect coupling 86.

By attaching the long extension 90 to the catheter body 82 with the quick connect coupling 86, a user can extend the working length of the catheter body 82 so that the length of the catheter body 82 is increased. In some embodiments, the length of the catheter body 82 can be approximately 100 cm or more. In some embodiments, the long extension 90 can be approximately 55 cm or greater in length, or between 50 cm or less and approximately 75 cm or more. In some embodiments, the catheter body 82 can be approximately 80 cm in length from the distal end of the catheter body 82 to the quick connect coupling 86.

In some embodiments, the quick connect coupling 86 can be configured to be insertable into a vessel within a body. In some embodiments, the quick connect coupling 86 can be configured to be pliable and also have indexing features so that the inflation lumen and guidewire lumen in the extension portion 88, 90 can be aligned with the inflation lumen and guidewire lumen in the catheter body 82 when the quick connect coupling is joined. The quick connect coupling can be sufficiently short to not create a long, stiffened section in the catheter body 82. The quick connect coupling 86 can be formed from one or more pliable materials. In some embodiments, the quick connect coupling 86 can be a snap fit connector or similar connector that can have indexing features to maintain the alignment of the lumens in the catheter body 82. In some embodiments, the quick connect coupling 86 can be a twist or threaded connector having indexing features to ensure the alignment of the guidewire and inflation lumens in the catheter body 82.

Figure 6:
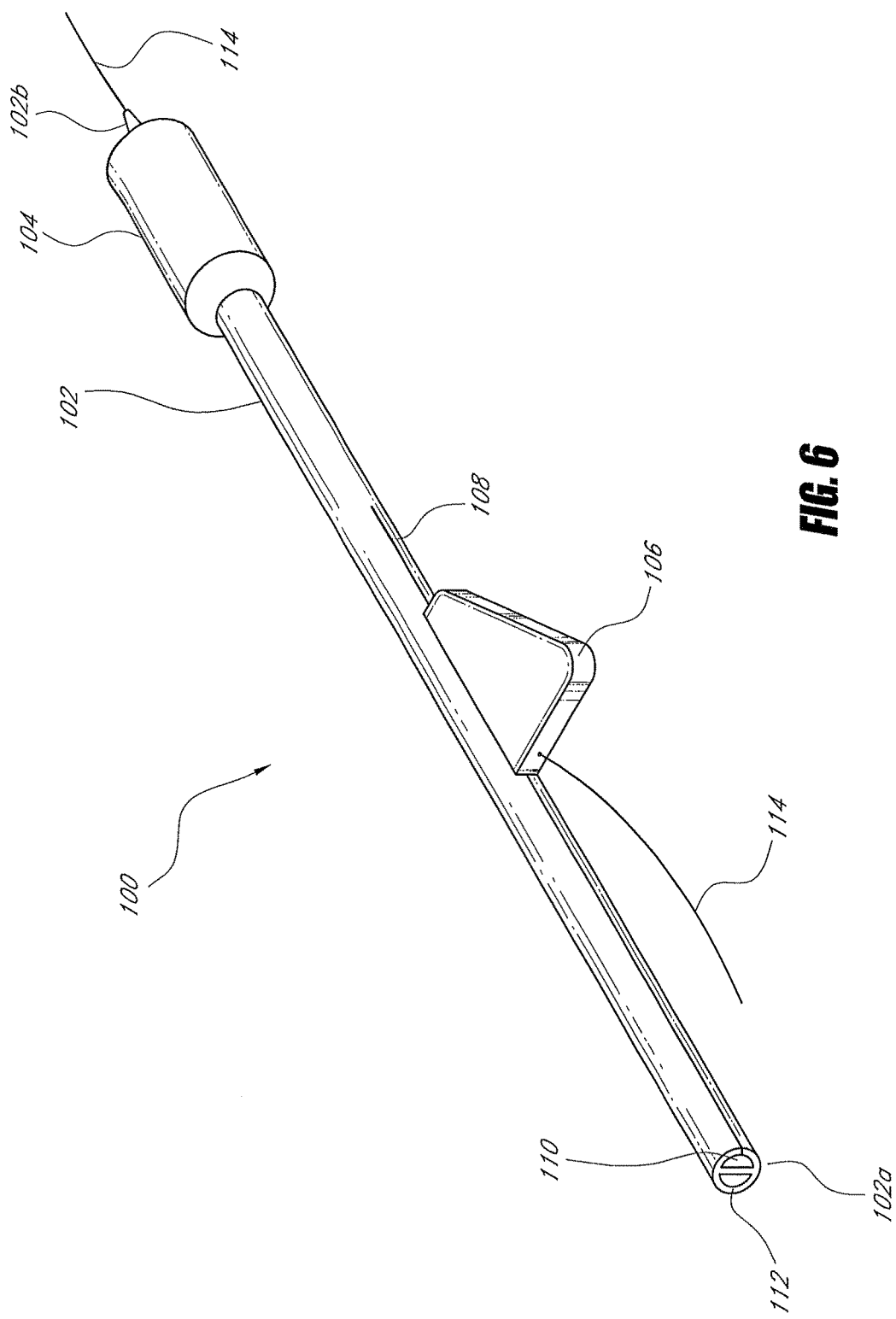
FIG. 6 is a perspective view of another embodiment of a catheter system.

FIG. 6 is a perspective view of another embodiment of a catheter system 100 having a catheter body 102, an inflation balloon 104, and a slider mechanism 106 (also referred to herein as a diverter). FIGS. 7-9 are a perspective view, a side view, and an end view, respectively, of the embodiment of the slider mechanism 106 shown in FIG. 6. The slider mechanism 106 can be configured to divert the guidewire 114 outside of a guidewire lumen 110. A typical over-the-wire inflation luer of the kind commonly found in the art can be attached to the proximal end 102a of the catheter body 102.

With reference to FIG. 6, a lengthwise slit 108 can be formed in the catheter body 102 between the outer surface of the catheter body 102 and the guidewire lumen 110, but not into the inflation lumen 112. The slit 108 can extend along the entire length of the catheter body 102, or along only a portion of the length of the catheter body 102. In some embodiments, the catheter body 102 can be configured such that the slit 108 is substantially self-sealing. Some embodiments of the slider mechanism 106 can have a first portion 106a sized and configured to be gripped by a user's hands or fingers, and a second portion 106b configured to be supported within a lumen of the catheter body 102. For example, in some embodiments, the slider mechanism 106 can be supported by the catheter system 100 such that the first portion 106a of the slider mechanism 106 can be located external to the catheter body 102 and guidewire lumen 110 while second portion 106b of the slider mechanism 106 can be slidably received within the guidewire lumen 110.

In some embodiments, the second portion 106b of the slider mechanism 106 can have a cross-sectional shape that is similar to the cross-sectional shape of the guidewire lumen 110. In some embodiments, the second portion 106b can have a tubular shape or have one or more curved surfaces. In some embodiments, the second portion 106b can have a flat bottom surface, such as the bottom surface 106c shown in FIG. 106b, to abut against a similarly shaped surface in the guidewire lumen 110. The flat bottom surface 106c can be configured to stabilize the slider mechanism 106 with respect to the catheter body 102 to inhibit movement of or rotation of the slider mechanism 106 relative to the catheter body 102 about a longitudinal axis of the catheter body 102. In some embodiments, the second portion 106b of the slider mechanism 106 can have a tubular or C-shaped cross-sectional shape. The first portion 106a of the slider mechanism 106 can be sized and shaped so that a user can easily grasp and manipulate the slider mechanism 106.

With reference to FIGS. 6-9, a guidewire 114 can be assembled with the catheter system 100 by advancing the guidewire 114 through the distal end 102b of the catheter body 102 and feeding the guidewire 114 through the guidewire lumen 110. Once the guidewire 114 reaches the slider mechanism 106, as mentioned, the slider mechanism 106 can divert the guidewire 114 outside of the guidewire lumen 110. The slider 106 can be distally or proximally advanced or translated until the desired position of the slider mechanism 106 is reached. After the guidewire 114 has been advanced through the catheter body 102 and the slider mechanism 106, a typical over-the-wire inflation luer fitting can be coupled with the proximal end 102a of the catheter body 102. In this arrangement, the guidewire 114 can remain within the guidewire lumen 110 of the portion of the catheter body 102 that can be inserted into the patient, and the working length of the catheter body 102 can be adjusted by sliding the slider 106 toward or away from the distal end of the catheter.

Figure 13B:
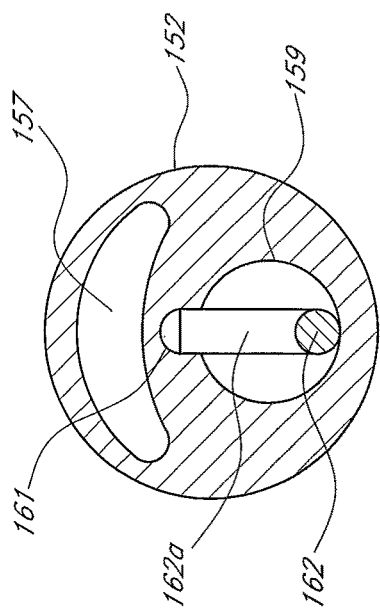
FIG. 13B is an enlarged section view of a portion of the embodiment of the catheter system shown in FIG. 10, defined by line 13B-13B shown in FIG. 13A.

FIG. 10 is a side view of another embodiment of a catheter system 150. FIG. 11 is a top view of an embodiment of the mandrel 162 shown in FIG. 10. FIG. 12 is a side view of an embodiment of the mandrel 162 shown in FIG. 10. FIG. 13A is an enlarged section view of a portion of the embodiment of the catheter system 150 shown in FIG. 10, defined by curve 13A-13A shown in FIG. 10. FIG. 13B is an enlarged section view of a portion of the embodiment of the catheter system 150 shown in FIG. 10, defined by line 13B-13B shown in FIG. 13A.

With reference to FIGS. 10-13B, the catheter system 150 can comprise a catheter body 152 having an inflation balloon 154, an inflation port 156 in communication with an inflation lumen 157, and a guidewire lumen 159 for receiving a guidewire 158. In some embodiments, the catheter body 152 can have some or all of the same features of any typical over the wire type catheter wherein the guidewire 158 can be advanced through the entire length of the catheter body 152 and exit through the proximal end 152a of the catheter body 152 when the mandrel 162 is not positioned in the guidewire lumen 159.

In the illustrated arrangement, the guidewire 158 can be advanced through a portion of the catheter body 152 so that the guidewire 158 exits through an opening 160 (also referred to herein as a port or notch) formed in the catheter body 152. In some embodiments, more than one opening 160 can be formed in the catheter body 152 or any other catheter body disclosed herein at any of a range of positions along the catheter body so that the guidewire 158 can exit the catheter body 152 at any of a wide range of locations. The mandrel 162 can be inserted into the catheter body 152 through the proximal end 152a of the catheter body and can be configured to help guide or deflect the guidewire 158 through the opening 160 if so desired. In some embodiments, the mandrel 162 can have a curved distal end 162a to divert the guidewire 158 through the opening 160 when oriented properly. In some embodiments, with reference to the mandrel 162 shown in FIG. 13A, the distal end portion 162a of the mandrel 162 can be beveled or slanted to divert the guidewire 158 from the guidewire lumen 159.

In some embodiments, the mandrel 162 and/or catheter body 152 can be indexed or keyed such as at the proximal end or along any portion of the length of the catheter body 152 to ensure the desired orientation of the mandrel 162 within the guidewire lumen 159 so that the guidewire 158 can exit smoothly. For example, with reference to FIG. 13B, the mandrel 162 and/or the guidewire lumen 159 through which the mandrel 162 is advanced can be keyed, indexed, or otherwise configured such that the beveled or angled end portion 162a of the mandrel 162 is biased to be in an optimal rotational orientation with respect to the opening 160. The end portion 162a can be angled by bending the end portion 162a of the mandrel 162. In some embodiments, an optimal rotational orientation with respect to the opening 160 can be one in which the end portion 162a of the mandrel 162 smoothly diverts the guidewire out of the opening 160 when the mandrel 162 has been advanced into the desired axial position within the guidewire lumen.

As illustrated in FIG. 13B, the guidewire lumen 159 can define a recess or channel 161 therein which can receive the end portion 162a therein or otherwise be configured to prevent the inadvertent rotation of the mandrel 162. In this configuration, the rotational or radial orientation of the mandrel 162 can be controlled. The channel 161 can be formed along all of or a portion of the length of the guidewire lumen 159.

Figure 13C:
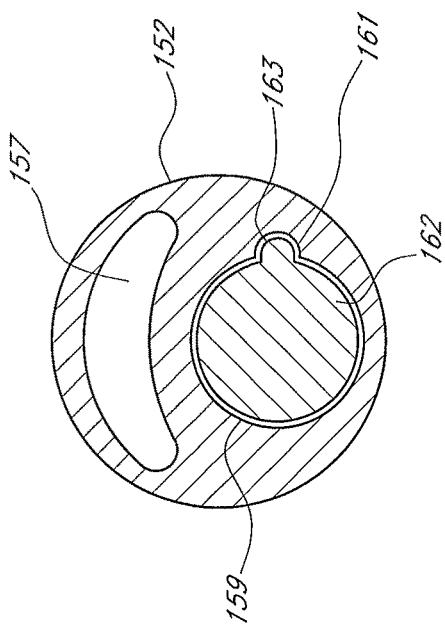
FIG. 13C is an enlarged section view of a portion of another embodiment of a catheter system, defined by line 13C-13C shown in FIG. 13A.
Figure 13A:
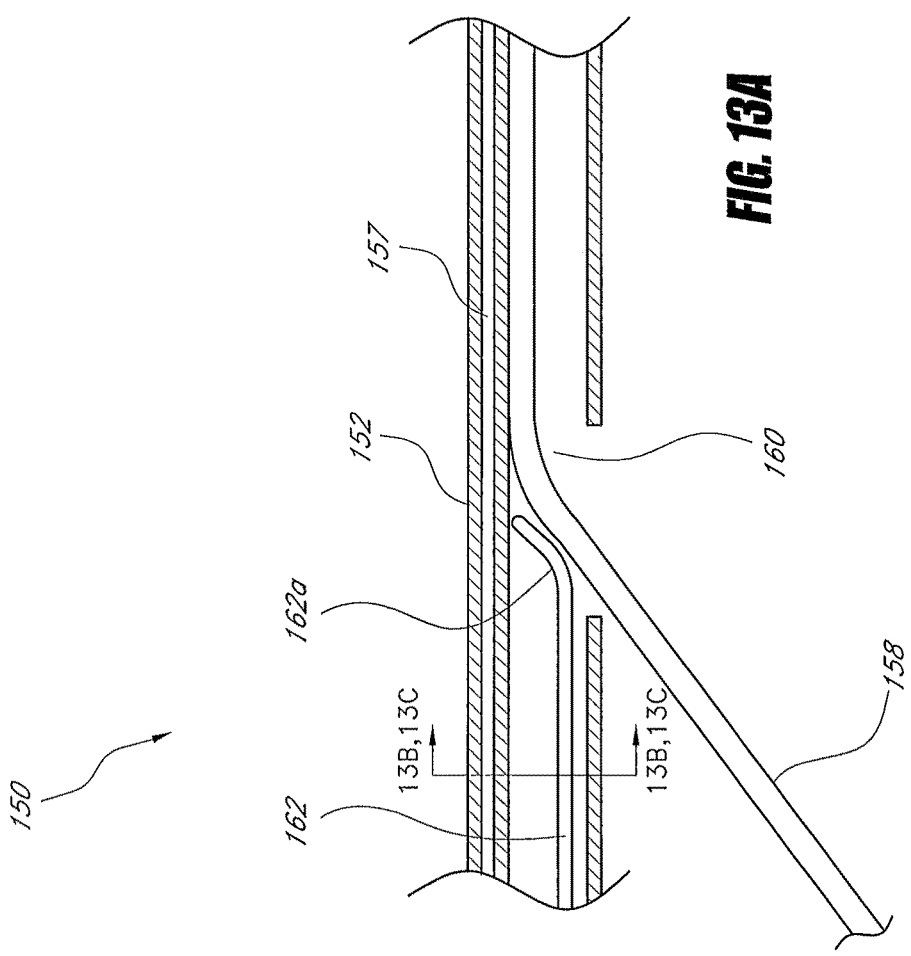
FIG. 13A is an enlarged section view of a portion of the embodiment of the catheter system shown in FIG. 10, defined by curve 13A-13A shown in FIG. 10.

Additionally, with reference to FIG. 13C, the guidewire lumen 159 can define a recess or channel 161 therein which can receive a ridge or protrusion 163 of the mandrel 162 therein or otherwise be configured to prevent the inadvertent rotation of the mandrel 162. The embodiment of the mandrel 162 illustrated in FIG. 13C can have a beveled or angled end portion (not illustrated) configured to divert a guidewire 158 through the opening 160 in the catheter body 152. In this configuration, the rotational or radial orientation of the mandrel 162 can be controlled. The channel 161 illustrated in FIG. 13C can be formed along all of or a portion of the length of the guidewire lumen 159.

In some embodiments, a handle 164 can be supported at the proximal end 162b of any embodiments of the mandrel 162 or other mandrels disclosed herein to assist the user in manipulation or removal of the mandrel. The handle 164 supported at the proximal end 162b of the mandrel 162 can also be keyed such that, when the handle is coupled with a feature on the proximal end 152a of the catheter 152, the mandrel's slanted or curved distal end 162a can be oriented to divert the guidewire 158 through the opening 160.

In some embodiments, the opening 160 can be positioned approximately 80 cm from the distal end 152b of the catheter body 152. In some embodiments, the opening 160 can be positioned at any desired or suitable location along the length of the catheter body 152. As mentioned above, when the mandrel 162 is removed from the guidewire lumen, the guidewire 158 can continue through the entire length of the catheter body 152 so that the entire length of the catheter body 152 can comprise a working length. In some embodiments, a cover or plug (not illustrated) can be positioned over the opening 160 to substantially cover the opening 160 when substantially the entire length of the catheter body 152 is desired to be inserted into the patient.

In some embodiments, the catheter body 152 can be strengthened or supported in the region of or adjacent to the opening 160 to prevent the catheter body 152 from buckling or kinking at or adjacent to the opening 160 due to the interruption of the outer surface of the catheter or the decrease in the cross-sectional area at the opening 160. In some embodiments, a solid mandrel or support can be inserted in the adjacent balloon inflation lumen or another lumen formed in the catheter body 152 to strengthen the catheter body 152 in the region of the opening 160. The mandrel or support can extend past the location of the opening 160, and can be removably or non-removably secured at the proximal end of the catheter using adhesive, welds, fasteners, or by any other suitable means. The mandrel can be tapered at the distal end or modified to reduce its stiffness to prevent the end of the wire from accidently perforating the lumen and exiting the catheter shaft.

In some embodiments (not illustrated), a removable clip can also be positioned on the outside of the catheter body 152 around or adjacent to the opening 160 to help the user locate the opening 160 and also assist in diverting the guidewire 158 out of the opening 160 when a shorter catheter length is desired. An interface mechanism, such as the sliding interface mechanism 32 described above, can also be attached to the catheter body 152 to permit the location of the inlet to the inflation lumen to be brought closer to the opening 160.

Figure 14A:
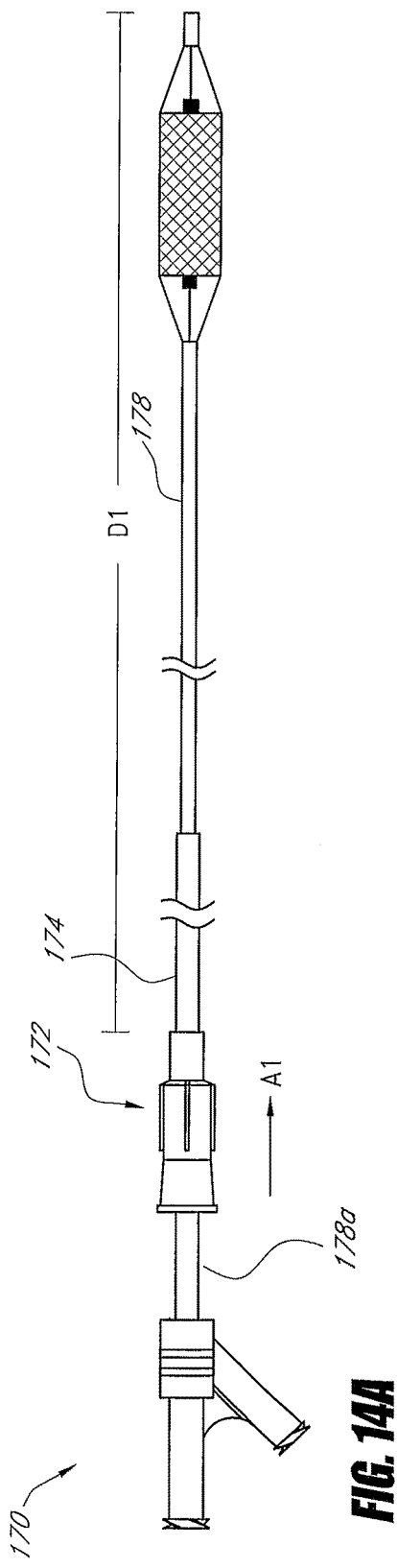
FIG. 14A is a side view of another embodiment of a catheter system, showing the catheter system in an extended configuration.
Figure 14B:
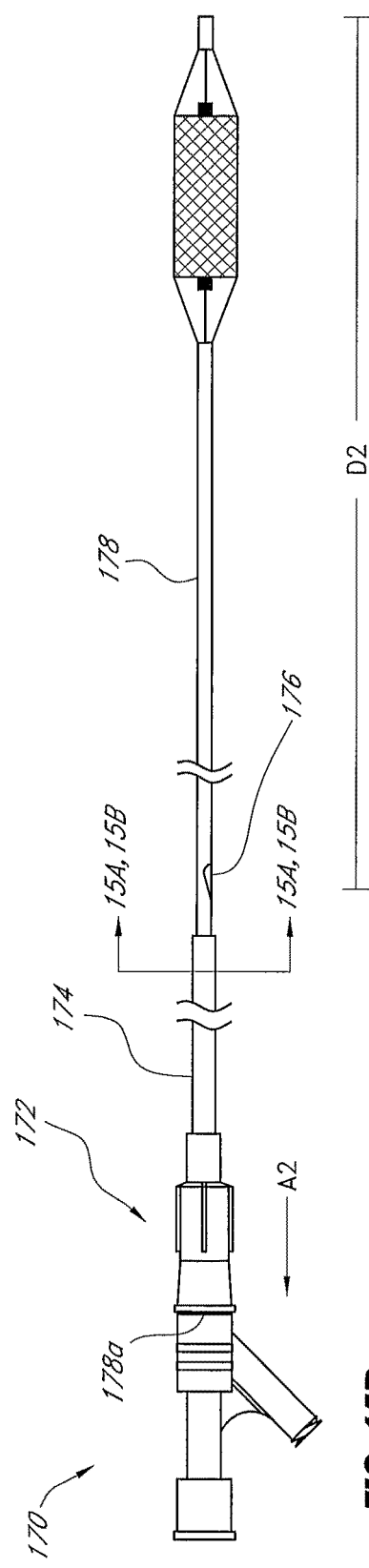
FIG. 14B is a side view of the embodiment of the catheter system shown in FIG. 14A, showing the catheter system in a shorter inserted length configuration.

FIGS. 14A and 14B are side views of another embodiment of a catheter system 170, showing an embodiment of a slideable assembly 172 incorporating an outer cover or sheath 174 that can be used to cover an opening 176 (also referred to herein as a port or notch) formed in the catheter body 178 when the longer length of the catheter is being used. Some embodiments of the catheter system 170 can have one or any combination of the same features, components, configurations, or details of any other catheter system embodiments disclosed herein. FIG. 14A shows the catheter system 170 in a longer inserted length configuration wherein the slideable assembly 172 has been axially advanced away from the proximal end 178a of the catheter body 178 such that the catheter system 170 is in an extended position. FIG. 14B shows the catheter system 170 in a shorter inserted length configuration wherein the slideable assembly 172 has been axially retracted to be positioned closer to the proximal end 178a of the catheter body 178 such that the catheter system 170 is in a shorter inserted length configuration. With reference to FIGS. 14A and 14B, the working length (i.e., the length that is designed to be insertable into the introducer sheath, or patient) of the catheter system 170 in the first or longer inserted length configuration (represented by D1 in FIG. 14A) is significantly greater than the working length of the catheter system 170 in the second or shorter inserted length configuration (represented by D2 in FIG. 14B).

In some embodiments of the catheter system 170 or any of the catheter system embodiments disclosed herein, the working length of the catheter system 170 in the first or longer inserted length configuration (represented by D1 in FIG. 14A) can be from 125 cm or less to approximately 150 cm or more, or from approximately 130 cm to approximately 140 cm, or from approximately 133 cm to approximately 137 cm, or to or from any values within these ranges. In some embodiments of the catheter system 170 or any of the catheter system embodiments disclosed herein, the working length of the catheter system 170 in the second or shorter inserted length configuration (represented by D2 in FIG. 14B) can be from 65 cm or less to approximately 100 cm or more, or from approximately 70 cm to approximately 90 cm, or from approximately 75 cm to approximately 85 cm, or to or from any values within these ranges.

In the extended position as shown in FIG. 14A, the sheath 174 of the slideable assembly 172 has been extended in the direction represented by arrow A1 in FIG. 14A so that the sheath 174 substantially covers the opening 176. In this position, the sheath 174 or any sheath of any other embodiment of the catheter system disclosed herein can provide additional structural support to the catheter body 178 at or adjacent to the position of the opening 176. Additionally, in some embodiments, the sheath 174 or any sheath of any other embodiment of the catheter system disclosed herein can be configured to provide a relatively fluid tight seal around the outside surface of the catheter body (such as, without limitation, catheter body 178). In some embodiments, with the sheath 174 or any other sheath herein positioned so as to cover the opening in the catheter body, the guidewire lumen can be used to inject fluids into the patient's vasculature.

In the shorter inserted length configuration, as illustrated in FIG. 14B, the sheath 174 of the slideable assembly 172 can be retracted in the direction represented by arrow A2 in FIG. 14B so that the sheath 174 does not cover the opening 176. In this position, a guidewire can pass through the opening 176. In some embodiments, the catheter system 170 can be configured such that a mandrel or other suitable device or feature can selectively divert a guidewire through the opening or opening 176.

In some embodiments, the slideable assembly 172 can be incorporated into any of the other catheters or catheter systems described herein or known in the field, including but not limited to the catheter system 150 or any other catheter system described herein. Further, in some embodiments, the catheter system 170 can have any of the components, features, or other details of any of the catheter systems disclosed herein or any other catheter systems known in the field.

In this arrangement, when the slideable assembly 172 has been advanced to cover the opening 176, as shown in FIG. 14A, the opening 176 can be substantially covered to prevent guidewires and other devices advanced through the proximal or distal end of the catheter lumen from inadvertently exiting the opening 176. When a shorter version of the catheter body 178 is preferred (or a shorter working length), the slideable assembly 172 can be retracted proximally (i.e., in the direction represented by arrow A2 in FIG. 14B) and an optional diverter rod (such as without limitation the mandrel 162 shown in FIG. 10 and described above) can be positioned in the guidewire lumen to divert the guidewire out of the opening 176. Then the catheter can be loaded onto the guide wire and advanced until the guide wire exits the opening 176. At this point, the guidewire and catheter 170 can be manipulated separately. As mentioned, when the longer version of the catheter system 170 is needed (e.g., a longer working length), the slideable assembly 172 can be extended distally to cover the opening 176 and the diverter rod can be removed. Then the catheter can be loaded onto the guide wire and advanced until the guide wire passes through the proximal end 178a of the catheter body 178.

In some embodiments, the opening 176 or any other port or notch herein can be positioned relative to the distal end of the catheter body 178 to ensure that a sufficient length of the catheter body 178 is provided distal of the opening 176. Positioning the opening 176 as described can ensure that the opening 176 remains outside of, i.e., proximal of, the introducer sheath when a guidewire is advanced through the opening 176. These features minimize the chance for tissue within the vasculature getting trapped between a guidewire and the body of the catheter 170 or the opening 176, which could lead to injury to the patient.

Figure 15A:
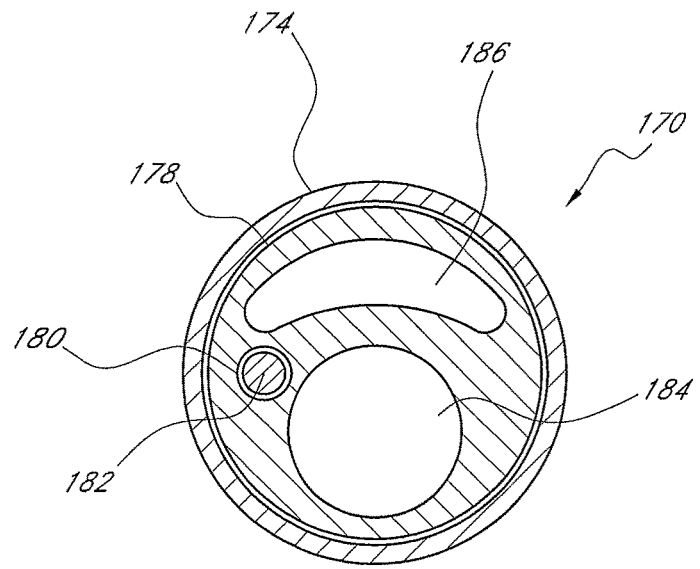
FIG. 15A is a section view of the embodiment of the catheter system shown in FIG. 14A, taken through line 15A-15A in FIG. 14B.
Figure 15B:
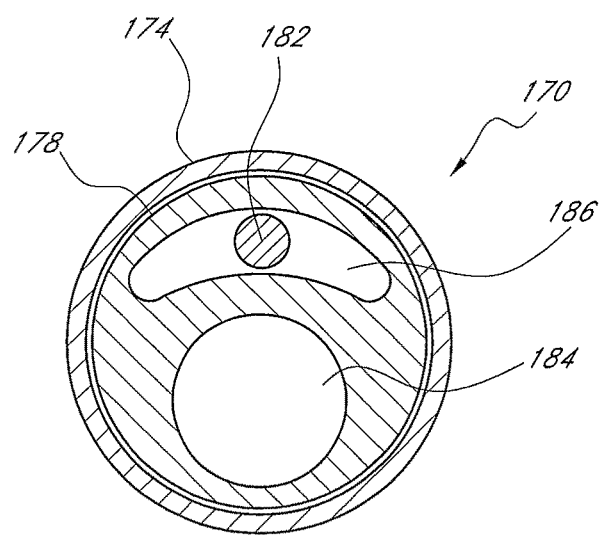
FIG. 15B is a section view of the embodiment of the catheter system shown in FIG. 14A, taken through line 15B-15B in FIG. 14B.

FIGS. 15A and 15B are section views of two embodiments of the catheter system shown in FIGS. 14A and 14B, taken through line 15A-15A in FIG. 14B. In some embodiments, as with any of the other embodiments of the catheters disclosed herein, the catheter body 178 can have a lumen 180 configured to removably or non-removably receive a stiffening mandrel or support 182 therein. The lumen 180 can be disposed parallel to the guidewire lumen 184. The stiffening mandrel 182 can be sized and configured to increase the strength and/or stiffness of the catheter body 178 adjacent to the opening 176. Alternatively, with reference to FIG. 15B, the catheter system 170 can be configured such that the stiffening mandrel or support 182 can be received within all or a portion of the inflation lumen 186 that can be formed in the catheter body 178. In any of the embodiments disclosed herein, the stiffening mandrel 182 can have a solid cross-section, a hollow cross-section, or any combination thereof.

Figure 16C:
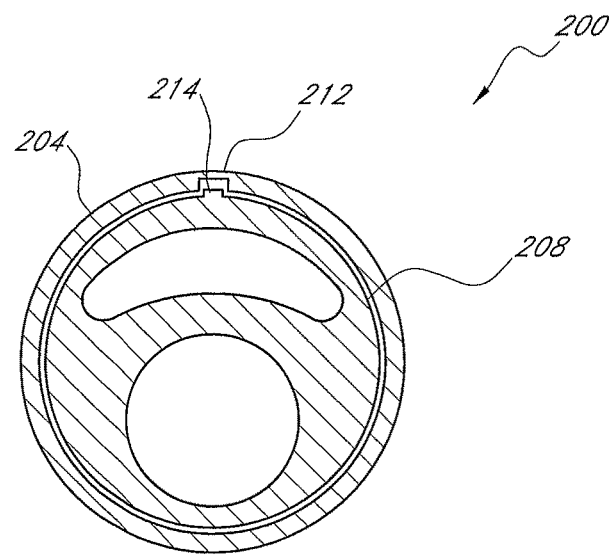
FIG. 16C is an enlarged section view of the embodiment of the catheter system shown in FIG. 16A, taken through line 16C-16C in FIG. 16A.

FIGS. 16A and 16B show another embodiment of a catheter system 200 that has a first or longer inserted length configuration and a second or shorter inserted length configuration, respectively. Some embodiments of the catheter system 200 can have one or any combination of the same features, components, configurations, or details of any other catheter system embodiments disclosed herein. The catheter system 200 can have a slideable assembly 202 incorporating an outer cover or sheath 204 that can be used to cover a notch or opening 206 formed in the catheter body 208 when the longer length of the catheter is being used. In some embodiments, the sheath 204 or, more particularly, the catheter body 208 can comprise more than one opening that can be independently exposed to provide the medical practitioner with a range of different working lengths of the catheter system 200. The catheter system 200 or any other catheter system herein can be configured such that the space between the sheath 204 and the catheter body 208 is substantially sealed or tight to prevent or inhibit any blood flow or other leakage between the sheath 204 and the catheter body 208.

FIG. 16A shows the catheter system 200 in a longer inserted length configuration wherein the slideable assembly 202 has been axially retracted toward the proximal end 208a of the catheter body 208 such that the catheter system 200 is in an extended position. FIG. 16B shows the catheter system 200 in a shorter inserted length configuration wherein the slideable assembly 202 has been axially advanced away from the proximal end 208a of the catheter body 208 such that the catheter system 200 is in a shorter inserted length configuration. In the retracted position as shown in FIG. 16A, the outer cover 206 of the slideable assembly 202 has been retracted in the direction represented by arrow A3 in FIG. 16A so that the notch or opening 210 (also referred to as a second opening) in the outer cover 206 is not aligned with the notch or opening 206 formed in the catheter body 208. In this position, where the openings 206, 210 are not aligned and the opening 206 is not exposed, the outer cover 206 can provide structural support to the catheter body 208 at or adjacent to the position of the opening 206.

In the axially advanced position, as illustrated in FIG. 16B, the sheath 204 of the slideable assembly 202 can be advanced in the direction represented by arrow A4 in FIG. 16B so that the opening 210 is aligned with and provides access through the sheath 204 to the opening 206. In this position, a guidewire can pass through the substantially aligned openings 206, 210. Advantageously, a portion of the sheath 204 adjacent to the opening 210 can provide some additional structural support at the axial position of the opening 206. In some embodiments, the catheter system 200 can be configured such that a mandrel or other suitable device or feature can selectively divert a guidewire through the opening 206 and 210. In some embodiments, instead of being axially movable, the sheath 204 of the slideable assembly 202 can be rotatable to align the openings 206, 210 or misalign the openings 206, 210.

In some embodiments, the slideable assembly 202 can be incorporated into any of the other catheters or catheter systems described herein or known in the field, including but not limited to the catheter system 150 or 170. Further, in some embodiments, the catheter system 200 can have any of the components, features, or other details of any of the catheter systems disclosed herein or any other catheter systems known in the field.

In this arrangement, when the slideable assembly 202 has been retracted to cover the opening 206, as shown in FIG. 16A, the opening 206 can be substantially covered to prevent guidewires and other devices advanced through the proximal or distal end of the catheter lumen from inadvertently exiting the opening 206. When a shorter working length version of the catheter body 208 is preferred, the slideable assembly 202 can be advanced distally (i.e., in the direction represented by arrow A4 in FIG. 16B). In some techniques, a diverter rod (such as without limitation the mandrel 162 shown in FIG. 10 and described above) can be positioned in the guidewire lumen to divert the guidewire out of the opening 206. Then the catheter can be loaded onto the guide wire and advanced proximally from a distal end port of the catheter body 208 until the guide wire exits the opening 206. At this point, the guidewire and catheter system 200 can be manipulated separately. As mentioned, when the longer version of the catheter system 200 is needed, the slideable assembly 202 can be extended distally to cover the opening 206 and the diverter rod can be removed. Then the catheter can be loaded onto the guide wire and advanced until the guide wire passes through the proximal end 208a of the catheter body 208.

In any of the embodiments disclosed herein, one or more of the components of the catheter system (for example, without limitation, the catheter system 200) can be indexed or otherwise configured to maintain the desired radial orientation, axial position, or otherwise of the components of the catheter system. For example, in some embodiments wherein the sheath 204 can be configured to be axially movable with respect to the catheter body 208, the sheath 204, catheter body 208, and/or other components of the catheter system 200 can have channels, depressions, protrusions, tabs, or other indexing or keying features to prevent the opening 210 formed in the sheath 204 from becoming radially misaligned with respect to the opening 206 formed in the catheter body 208.

For example, an inside surface of the sheath 204 can define a channel 212 longitudinally formed therein along at least a portion of the length of the sheath 204, and an outer surface of the catheter body 208 can have a protrusion or tab 214 formed thereon configured to engage with the channel 212 formed in the sheath 204. In an alternative embodiment (not illustrated), the tab (such as the tab 214) can be disposed on the sheath 204 and the channel (such as channel 212) can be disposed on the catheter body 208. In these configurations, to align the respective openings 206, 210, the medical practitioner need only be concerned with the axial positioning of the openings 206, 210 and may align these components merely by changing the axial position of the sheath 204 with respect to the catheter body 208.

In any of the embodiments disclosed herein, although not required, one or more of the components of the catheter system (for example, without limitation, the catheter system 200 described above) can have depressions or detents or other biasing or indicating features formed therein. The depressions, detents, or other biasing or indicating features can be configured to selectively bias the relative components such as the sheath 204 and the catheter body 208 in one of two or more desired positions relative to one another.

Figure 16D:
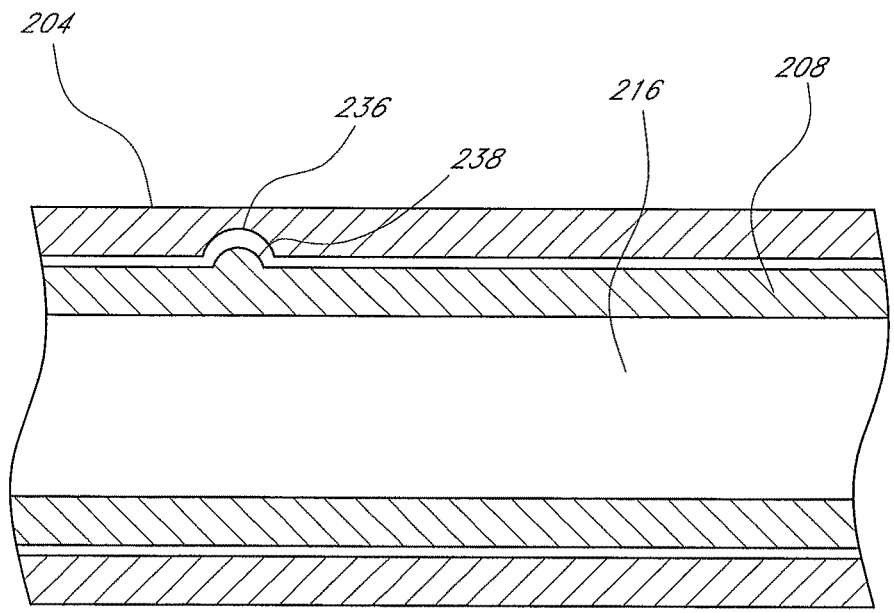
FIG. 16D is an enlarged section view of the embodiment of the catheter system shown in FIG. 16A, taken through line 16D-16D in FIG. 16B.

FIG. 16D is an enlarged section view of the embodiment of the catheter system 200 shown in FIG. 16A, taken through line 16D-16D in FIG. 16B. The section view defined by FIG. 16D is taken through the inflation lumen 216 of the catheter body 204. With reference to FIG. 16D, an inside surface of the sheath 204 can define one or more depressions or detents 236 formed therein at various locations on the inside surface of the sheath 204, and an outer surface of the catheter body 208 can have a rounded or otherwise shaped protrusion or tab 238 formed thereon configured to selectively engage with one of the depression or depressions 236 formed in the sheath 204. In an alternative embodiment (not illustrated), the tab or protrusion 238 can be disposed on the sheath 204 and the depression or depressions 236 can be disposed on the catheter body 208. The depressions and protrusions, or other similar features can be located at a variety of predetermined radial or longitudinal locations, depending on whether the sheath 204 is axially movable, radially movable, or movable in both the axial and radial directions with respect to the catheter body 208.

In this arrangement, the depressions or other biasing or indicating features formed in the sheath 204 and/or catheter body 208 can provide the user (which may be a medical practitioner) with a physical indication, e.g., a tactile feedback, of the relative positioning of the sheath 204 and the catheter body 208. The tactile feedback provided to the user that can indicate the relative positioning of the outer sleeve and the catheter body can be achieved not only by indicating features formed in the outer sleeve or catheter body, but also by configuring a proximal handle of any embodiments of the catheter systems disclosed herein to incorporate a spring that forces a button into one of two or more slots. For example, a first slot could be configured for a distal sleeve position (i.e., a long catheter configuration) and a second slot could be configured for a proximal sleeve position (i.e., a short catheter configuration).

In some embodiments, one depression 236 can be formed in the sheath 204 at one position associated with the first or longer inserted length configuration of the catheter system 200, while another depression 236 can be formed in the sheath 204 at a second position associated with the second or shorter inserted length configuration of the catheter system 200. A protrusion or tab 238 formed in the catheter body 208 can be configured to engage with each one of the two or more depressions 236 that can be formed in the sheath 204 so that the medical practitioner can feel when the sheath 204 has been positioned in the desired axial or radial position relative to the catheter body 208. Additionally, these features can be configured to bias the sheath 204 to remain in the selected axial or radial position with respect to the catheter body 208.

In any of the embodiments disclosed herein, the opening 206 or any other notch or port disclosed herein can be positioned relative to the distal end of the catheter body 208 to ensure that a sufficient length of the catheter body 208 is provided distal of the opening 206. In some embodiments, positioning the opening 206 as described can ensure that the opening 206 does not enter the introducer sheath or the patient's vasculature when a guidewire is advanced through the opening or opening 206, thus preventing potential injury to the patient from the guidewire.

Figure 17C:
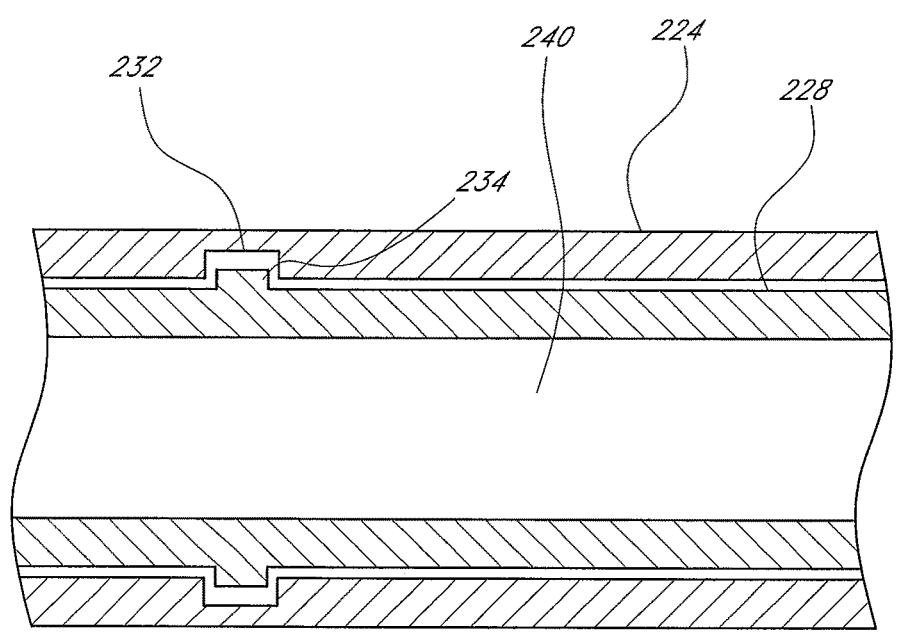
FIG. 17C is an enlarged section view of the embodiment of the catheter system shown in FIG. 17A, taken through line 17C-17C in FIG. 17B.

FIG. 17A is a side view of another embodiment of a catheter system 220, showing the catheter system 220 in a first configuration. FIG. 17B is a side view of the embodiment of a catheter system 220 shown in FIG. 17A, showing the catheter system 220 in a second configuration. FIG. 17C is an enlarged section view of the embodiment of the catheter system 220 shown in FIG. 17A, taken through line 17C-17C in FIG. 17B. The section view defined by FIG. 17C is taken through the inflation lumen 240 of the catheter body 224. In some embodiments, the catheter system 220 can have any of the features, components, or details of any of the other catheter systems disclosed herein, such as catheter system 200, in addition to or the alternative to, any of the features described below or illustrated in the figures.

In some embodiments, such as illustrated in FIGS. 17A-17C, the sheath 224 can be configured to be radially or rotationally movable with respect to the catheter body 228 to align the openings 226, 230. For example, the rotatable assembly 222 can be rotated to rotate the sheath 224 and, hence, the opening 230 formed in the sheath 224. Additionally, the sheath 224, catheter body 228, and/or other components of the catheter system 220 can have channels, depressions, protrusions, tabs, or other indexing or keying features to prevent the opening 230 formed in the sheath 224 from becoming axially misaligned with respect to the opening 226 formed in the catheter body 228. For example, with reference to FIG. 17C, an inside surface of the sheath 224 can define a channel 232 partially or fully circumferentially formed therein, and an outer surface of the catheter body 228 can have a protrusion or tab 234 formed thereon configured to engage with the channel 232 formed in the sheath 224.

Similar to the catheter system 200, in some embodiments, the catheter system 210 can have depressions or detents or other biasing or indicating features formed therein. The depressions, detents, or other biasing or indicating features can be configured to selectively bias the relative components such as the sheath 224 and the catheter body 228 in one of two or more desired positions relative to one another. In some embodiments, the channel 232 can have protrusions, tabs, stops, or other similar features to limit the degree of rotation of the sheath 224 relative to the catheter body 228, or to assist with aligning the openings 226, 230.

In an alternative embodiment (not illustrated), the tab 234 can be disposed on the sheath 224 and the channel 232 can be disposed on the catheter body 228. In this configuration, to align the respective openings 226, 230, the medical practitioner need only be concerned with the radial or rotational positioning of the openings 226, 230 and can align the openings 226, 230 by changing the radial position of the sheath 224 with respect to the catheter body 228. The radial position of the sheath 224 with respect to the catheter body 228 and, hence, the radial position of the opening 230 with respect to the opening 226, can be adjusted by rotating the sheath 224 about a longitudinal axis of the catheter body 208.

FIGS. 18A and 18B are side views of another embodiment of a catheter system 260, showing an embodiment of a slideable assembly 262 incorporating an outer cover or sheath 264 that can be used to cover an opening 266 (also referred to herein as a port or notch) formed in the catheter body 268 when the longer length of the catheter is being used. Some embodiments of the catheter system 260 can have one or any combination of the same features, components, configurations, or details of any other catheter system embodiments disclosed herein. FIG. 18A shows the catheter system 260 in a longer inserted length configuration wherein the slideable assembly 262 has been axially advanced away from the proximal end 268a of the catheter body 268 such that the catheter system 260 is in an extended position. FIG. 18B shows the catheter system 260 in a shorter inserted length configuration wherein the slideable assembly 262 has been axially retracted to be positioned closer to the proximal end 268a of the catheter body 268 such that the catheter system 260 is in a shorter inserted length configuration. Some embodiments of the catheter system 300 can have one or any combination of the same features, components, configurations, or details of any other catheter system embodiments disclosed herein.

In the extended position as shown in FIG. 18A, the sheath 264 of the slideable assembly 262 has been extended in the direction represented by arrow A5 in FIG. 18A so that the sheath 264 substantially covers the opening 266. In this position, the sheath 264 or any sheath of any other embodiment of the catheter system disclosed herein can provide additional structural support to the catheter body 268 at or adjacent to the position of the opening 266. Additionally, in some embodiments, the sheath 264 or any sheath of any other embodiment of the catheter system disclosed herein can be configured to provide a relatively fluid tight seal around the outside surface of the catheter body (such as, without limitation, catheter body 268). In some embodiments, with the sheath 264 positioned so as to cover the opening 266 in the catheter body, the guidewire lumen can be used to inject fluids into the patient's vasculature.

In the shorter inserted length configuration, as illustrated in FIG. 18B, the sheath 264 of the slideable assembly 262 can be retracted in the direction represented by arrow A6 in FIG. 18B so that the sheath 264 does not cover the opening 266. In this position, a guidewire can pass through the opening 266. As will be described, the catheter system 260 can be configured such that, when the catheter system 260 is in the shorter inserted length configuration such as shown in FIG. 18B, a mandrel or other diverting device is not required to divert a guidewire through the opening or opening 266. Rather, the angulation of the catheter body 268 adjacent to the opening 266 can bias a guidewire toward the opening 266 without the use of a mandrel or diverter.

In this arrangement, when the slideable assembly 262 has been advanced to cover the opening 266, as shown in FIG. 18A, the opening 266 can be substantially covered to prevent guidewires and other devices advanced through the proximal or distal end of the catheter lumen from inadvertently exiting the opening 266. When a shorter version or working length of the catheter body 268 is preferred, the slideable assembly 262 can be retracted proximally (i.e., in the direction represented by arrow A6 in FIG. 18B). The catheter system 260 can be configured such that, in the shorter inserted length configuration as illustrated in FIG. 18B, the catheter body 268 is configured to bend or curve upwardly (for example, without limitation, such that the catheter bends in a direction that is away from the opening 266) in the portion of the catheter body 268 adjacent to the opening 266. In some embodiments, the catheter body 268 can bend or curve about an inflection point. The inflection point can be adjacent to a center point or an end point of the opening 266.

In some embodiments, the catheter body 268 can be substantially linear (in a relaxed state) along the lengths of the catheter body 268 proximal to and distal of the opening 266. In this configuration, as the catheter system 260 is being advanced over a guidewire 270, due to the curvature of the catheter body 268 adjacent to the opening 266, the guidewire can be directed out of the opening 266 without the use of a mandrel or diverter positioned within the proximal portion of the guidewire lumen.

The catheter body 268 can be configured to be biased to curve upwardly adjacent to the opening 266 in any of a number of different ways. In some embodiments, a preformed, shaped mandrel, such as, without limitation, the shaped mandrel 272 shown in FIG. 18C, can be embedded or otherwise positioned within the catheter body 268 so as to bias the catheter body 268 to curve upwardly adjacent to the opening 266. As illustrated in FIG. 18C, the shaped mandrel 272 can have a curve or angle 274 configured to coincide with the location of the opening 266 formed in the catheter body 268 when the mandrel 272 has been positioned within the catheter body 268.

In some embodiments, the catheter body 268 can be configured such that, when the catheter is in the shorter inserted length configuration, as shown in FIG. 18B, the angle of curvature of the catheter body 268 at or adjacent to the opening 266 (represented by angle X as shown in FIG. 18B) can be approximately 30 degrees relative to the proximal portion of the catheter body 268. In some embodiments, the angle of curvature of the catheter body 268 at or adjacent to the opening 266 can be from approximately 5 degrees or less to approximately 30 degrees or more, or from approximately 30 degrees to approximately 50 degrees relative to the proximal portion of the catheter body 268. Additionally, in some embodiments, the desired angle of curvature of the catheter body 268 at or adjacent to the opening 266 can be selected based on the size of the opening 266 formed in the catheter body 268, the size of the guidewire to be advanced through the opening 266, and/or the smallest bend radius that can be substantially straightened by advancing the sheath 264 thereover. Therefore, in some embodiments, the angle of the catheter body 268 in the first position can be greater than the angle of the catheter body 268 in the second position. The angle of the catheter body 268 in the first position can be substantially greater than the angle of the catheter body 268 in the second position.

In some embodiments, the opening 266 can be configured such so that the angle required to divert a guidewire out of the guidewire lumen can be minimized. For example, without limitation, a proximal portion of the opening 266 can be angled or beveled so that a guidewire exiting the opening 266 when the catheter body 268 is in an angled (i.e., first configuration), the guidewire will not be obstructed from exiting the opening 266 by the sidewall of the catheter body 268.

As discussed in greater detail below, in some embodiments, a removable mandrel (not illustrated) can move the catheter body 268 between the first and second configurations. The mandrel can have a predetermined angle at an inflection point that can correspond with the inflection point of the catheter body.

Accordingly, in some embodiments, the shaped mandrel can be positioned within an inflation lumen of the catheter body 268, imbedded within the wall of the catheter body, or positioned within a separate lumen configured to receive the shaped mandrel. The shaped mandrel can be formed from Nitinol heat set in the angled shape, or from stainless steel or any other suitable material. In some embodiments, the catheter body 268 can be formed or heat set to have the desired angle adjacent to the opening 266 so that an angled or shaped mandrel is not required.

The catheter body 268 can be configured such that, when the longer inserted length configuration of the catheter body 268 is desired, such as is illustrated in FIG. 18A, the slideable assembly 262 can be extended distally in the direction A5 so that the sheath 264 covers the opening 266. In some embodiments, though not required, the sheath 264 can be configured to overcome the angled or curved bias of the catheter body 268 to substantially straighten the catheter body 268 as the sheath 264 is being advanced over the opening 266 in the catheter body 268. Additionally, in some embodiments, a mandrel can be advanced through a lumen in the catheter body, such as the inflation lumen, to substantially straighten the catheter body 268 adjacent to the opening 266, when the longer inserted length configuration is desired. However, in some embodiments, the catheter system 260 can be configured such that the catheter body 268 remains at least partially curved or angled adjacent to the opening 266 in the longer inserted length configuration. Then the catheter can be loaded onto the guide wire and advanced until the guide wire passes through the proximal end 268a of the catheter body 268. In some embodiments, a user can move the catheter body 268 with his or her hands to change the catheter body 268 from an angled configuration to an approximately straight configuration. The catheter body 268 can be configured to be biased to remain in either the angled or the straight configuration.

In some embodiments, the opening 266 or any other port or notch herein can be positioned relative to the distal end of the catheter body 268 to ensure that a sufficient length of the catheter body 268 is provided distal of the opening 266. Positioning the opening 266 as described can ensure that the opening 266 remains outside of (i.e., proximal of) the introducer sheath when a guidewire is advanced through the opening 266, and throughout a procedure in some cases. These features minimize the chance for tissue within the vasculature getting trapped between a guidewire and the body of the catheter 260 or the opening 266, which could lead to injury to the patient.

Figure 19:
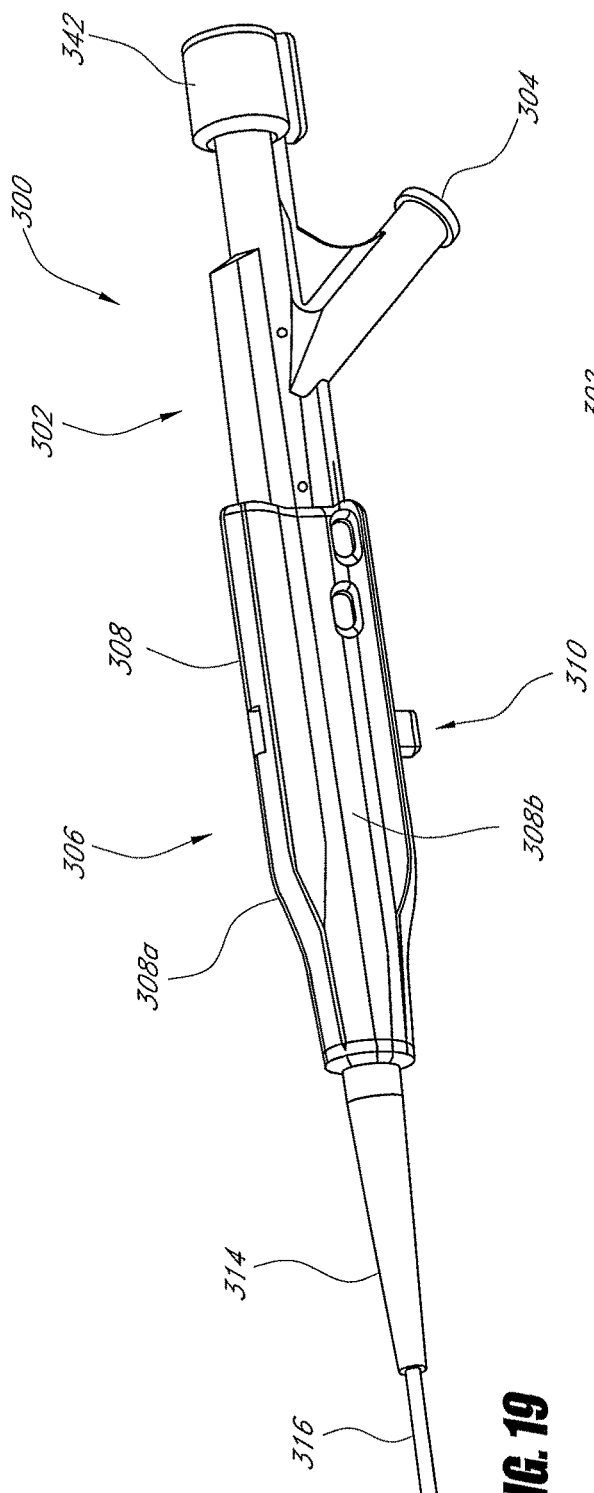
FIG. 19 is a perspective view of another embodiment of a catheter system.

FIG. 19 is a perspective view of another embodiment of a catheter system 300. Some embodiments of the catheter system 300 can have one or any combination of the same features, components, configurations, or details of any other catheter system embodiments disclosed herein. As illustrated FIG. 19, the catheter system can have a catheter body 302 having an inflation port 304 in communication with an inflation lumen, and a guidewire lumen for receiving a guidewire. In some embodiments, the catheter body 302 can be curved or angled, such as with the embodiment of the catheter body 268 described above, or in some embodiments, the catheter body 302 can be can be straight, as described above. A slider mechanism 306 having a housing 308 and a release mechanism 310 can be supported by the catheter body 302. The housing 308 can have a first cover 308a and a second cover 308b that can be held together about the catheter body 302 using adhesive, snap fit features, press fit features, sonic welds, or other suitable components or features.

Figure 20:
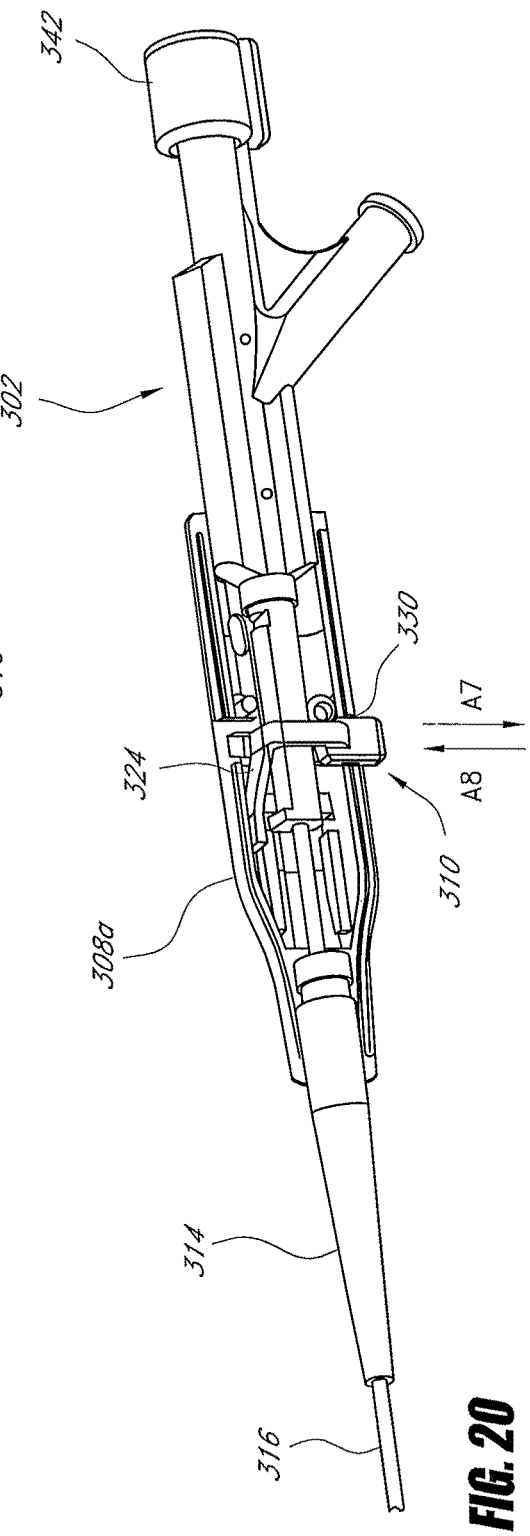
FIG. 20 is a perspective view of the embodiment of a catheter system shown in FIG. 19, with a portion of the housing removed for clarity.
Figure 21:
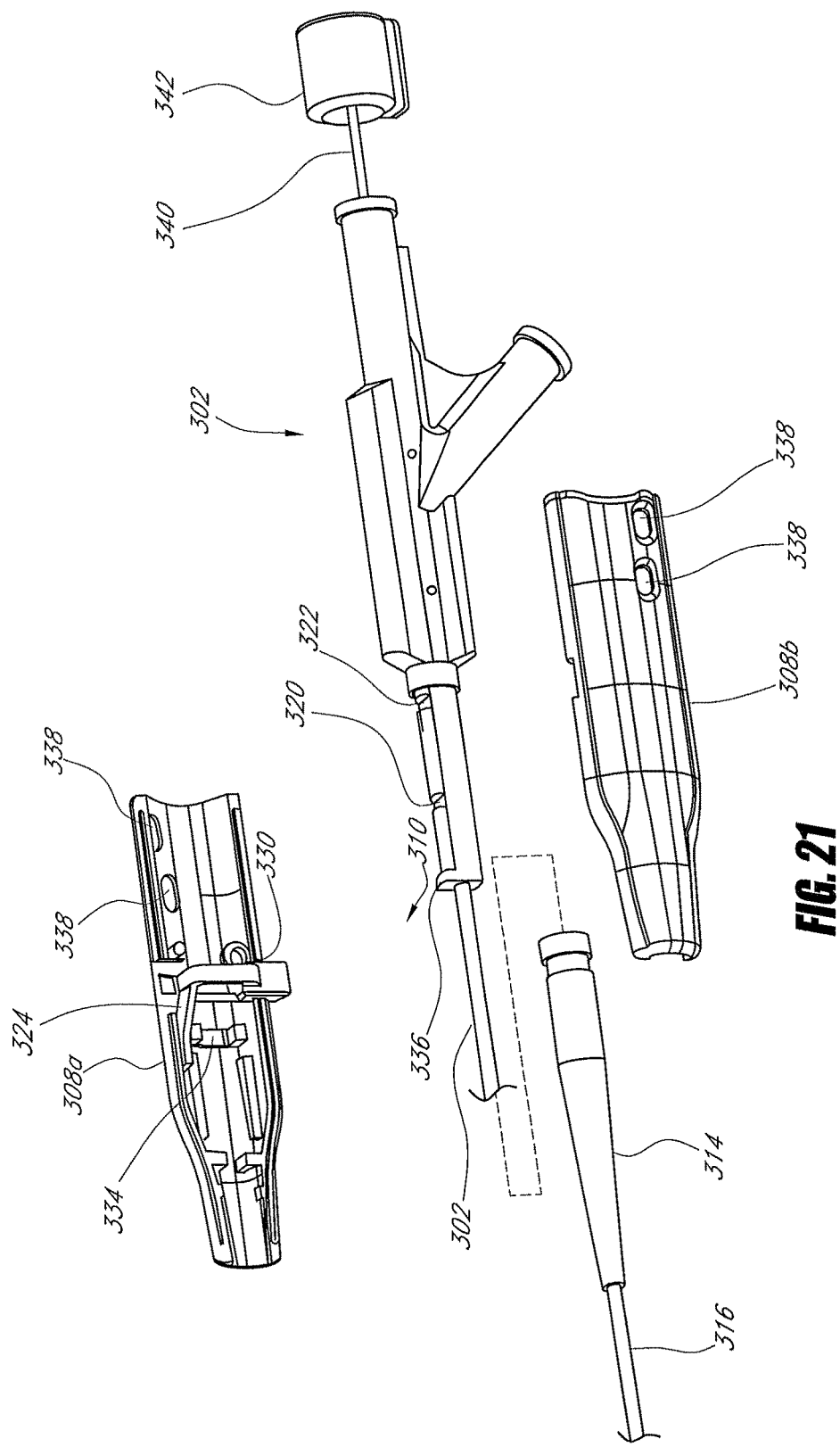
FIG. 21 is an exploded view of the embodiment of a catheter system shown in FIG. 19.

FIG. 20 is a perspective view of the embodiment of a catheter system 300, with the second cover 308b removed for clarity. FIG. 21 is an exploded view of the catheter system 300. With reference to FIGS. 19-21, the slider mechanism 306 can have a tip member 314 that can project from the distal end portion of the housing 308. The tip member 314 can provide additional support to the catheter body 302 to substantially prevent the catheter body 302 from kinking or collapsing at a position that is distal of the housing 308. The tip member 314 can be strain relief device of any suitable configuration. Additionally, the slider mechanism 306 or the tip member 314 can support an outer sheath 316, which can project distally from the end of the tip member 314. With reference to FIG. 20, in some embodiments, the tip member 314 can be radially and axially supported within the housing 308 such that the tip member 314 and the outer sheath are substantially prevented from translating in an axial direction relative to the housing 308. In some embodiments, the housing 308 and/or tip member 314 can have annular protrusions, annular channels, tabs, depressions, or other features to substantially prevent the tip member 314 and the outer sheath from translating in the axial direction relative to the housing 308. In this arrangement, the tip member 314 and the outer sheath 316 can move with the housing 308 and other components of the slider mechanism 306 when the slider mechanism 306 is moved between at least a first and a second position.

The outer sheath 316 can be configured to extend over an outside surface of the portion of the catheter body 302 that extends distally beyond the housing 308. Similar to other embodiments of catheter systems disclosed herein, the outer sheath 316 can be configured to translate axially between at least a first and a second position so as to selectively expose or cover an opening (not illustrated) in the catheter body 302 through which a guidewire (not illustrated) can be advanced. For example, when slider mechanism is translated to the first position such that the catheter system 300 is in a first or longer inserted length configuration, the sheath 316 can cover the opening in the catheter body 302. In this configuration, a guidewire can be advanced proximally past the opening in the catheter body 302 and continue through the guidewire lumen to the proximal end of the catheter body 302. Alternatively, when slider mechanism is translated to the second position such that the catheter system 300 is in a second or shorter inserted length configuration, the sheath 316 can expose the opening in the catheter body 302 so that a guidewire can be advanced through the opening in the catheter body so as to exit the catheter body 302 through the opening.

As will be described, the slider mechanism 306 can be moved from a first position, as illustrated in FIG. 20 wherein the slider mechanism 306 is in a forward position relative to the catheter body 302, to a second position (not illustrated) wherein the slider mechanism 306 is in a rearward position relative to the catheter body 302. In some embodiments, the slider mechanism 306 can be configured to engage with at least two channels 320, 322 formed in the catheter body 302. The slider mechanism 306 is in the first or forward position when engaged with channel 320 (as illustrated in FIG. 20), and is in the second or rearward position when engaged with channel 322. With reference to FIG. 21, the release mechanism 310 that is supported within the housing 308 can be configured to selectively engage with the channels 320, 322. A spring member 324, which can be a cantilevered spring member, can bias a tab or other protrusion (not illustrated) supported by the release mechanism 310 in the direction defined by arrow A7 shown in FIG. 20 to selectively engage with the channels 320, 322.

A portion of the release mechanism 310 can project through an opening 330 in the housing 308 so that a user can depress the release mechanism 310 against the bias of the spring member 324, so that the housing 308 and the sheath 316 can be translated axially between at least the first and second positions. In this arrangement, a user can depress the release mechanism 310 in the direction defined by arrow A8 in FIG. 20 to allow the housing 308 to slide or translate axially relative to the catheter body 302. Channels, protrusions, or other features, such as the channels 334 formed on the inside of the housing 306 can be configured to engage with or receive the catheter body 302 to provide increased support to the housing 308 as the housing 308 is translated relative to the catheter body 302. Additionally, in some embodiments, a stop or tab 336 can be formed on the catheter body 302 to prevent the over-translation of the housing 308 relative to the catheter body 302.

In some embodiments, openings 338 can be formed in the housing 308 to allow a user to view the position of the housing 308 relative to the catheter body 302, or to view other aspects of the catheter body 302. Further, in some embodiments, the catheter system 300 can support a mandrel 340 having a handle portion 342. The mandrel 340 can be advanceable within a lumen formed in the catheter body 302, such as an inflation lumen or separate lumen configured to receive the mandrel 340. The mandrel 340 can have any of the same features or shapes of any of the other mandrels disclosed herein.

FIG. 22 is a perspective view of another embodiment of a catheter system 400. Some embodiments of the catheter system 400 can have one or any combination of the same features, components, configurations, or details of any other catheter system embodiments disclosed herein. As illustrated FIG. 22, the catheter system can have a catheter body 402 having an inflation port 404 in communication with an inflation lumen, and a guidewire lumen for receiving a guidewire. In some embodiments, the catheter body 402 can be curved or angled, such as with the embodiment of the catheter body 268 described above, or in some embodiments, the catheter body 402 can be can be straight, as described above. A slider mechanism 406 can be supported within a housing 408. The slider mechanism can have a release mechanism 410 configured to selective secure the slider mechanism 406 in the axial direction in one of two or more predetermined positions. The housing 408 can have a first cover 408a and a second cover 408b that can be held together about the catheter body 402 using adhesive, snap fit features, press fit features, sonic welds, or other suitable components or features.

Figure 24:
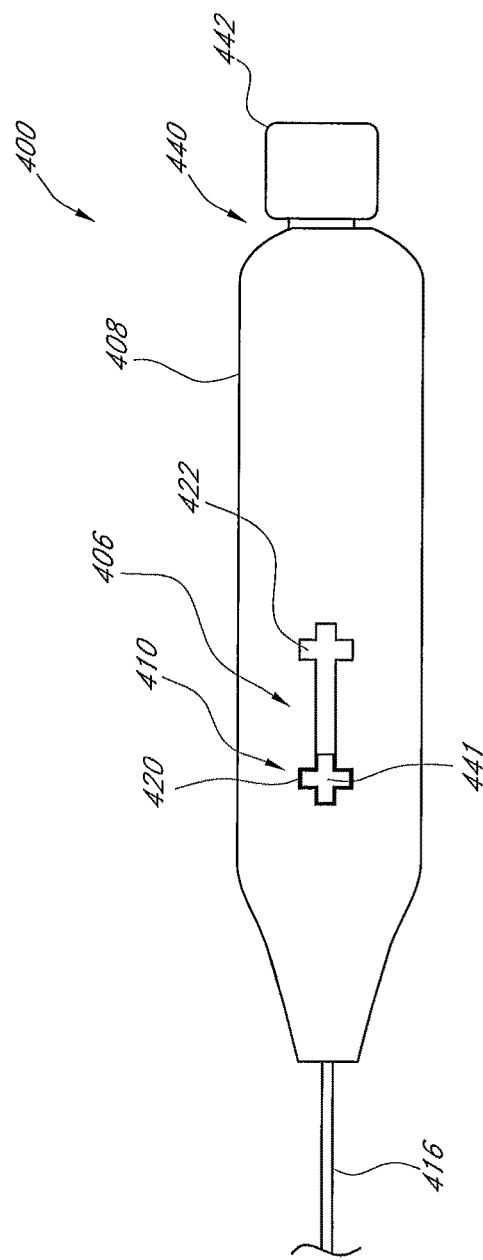
FIG. 24 is a top view of the embodiment of a catheter system shown in FIG. 22

FIGS. 23 and 24 are a perspective view and a top view, respectively, of the embodiment of a catheter system 400, with the second cover 408b removed for clarity. With reference to FIGS. 22-23, the slider mechanism 406 can have a tip member or strain relief device (not illustrated) that can be similar to the tip member 314 described above that can project from the distal end portion of the housing 408. The tip member can provide additional support to the catheter body 402 to substantially prevent the catheter body 402 from kinking or collapsing at a position that is distal of the housing 408. Additionally, the slider mechanism 406 can support an outer sheath 416, which can project distally from the end of the tip member. In some embodiments, the tip member can be radially and axially supported within the housing 408 such that the tip member and the outer sheath are substantially prevented from translating in an axial direction relative to the housing 408. In some embodiments, the housing 408 and/or tip member can have annular protrusions, annular channels, tabs, depressions, or other features to substantially prevent the tip member and the outer sheath from translating in the axial direction relative to the housing 408. In this arrangement, the tip member and the outer sheath 416 can move with the housing 408 and other components of the slider mechanism 406 when the slider mechanism 406 is moved between at least a first and a second position.

The outer sheath 416 can be configured to extend over an outside surface of the portion of the catheter body 402 that extends distally beyond the housing 408. Similar to other embodiments of catheter systems disclosed herein, the outer sheath 416 can be configured to translate axially between at least a first and a second position so as to selectively expose or cover an opening (not illustrated) in the catheter body 402 through which a guidewire (not illustrated) can be advanced. For example, when slider mechanism is translated to the first position such that the catheter system 400 is in a first or longer inserted length configuration, the sheath 416 can cover the opening in the catheter body 402. In this configuration, a guidewire can be advanced proximally past the opening in the catheter body 402 and continue through the guidewire lumen to the proximal end of the catheter body 402. Alternatively, when slider mechanism is translated to the second position such that the catheter system 400 is in a second or shorter inserted length configuration, the sheath 416 can expose the opening in the catheter body 402 so that a guidewire can be advanced through the opening in the catheter body so as to exit the catheter body 402 through the opening.

As will be described, the slider mechanism 406 can be moved from a first position, as illustrated in FIG. 23 wherein the slider mechanism 406 is in a forward position relative to the catheter body 402, to a second position (not illustrated) wherein the slider mechanism 406 is in a rearward position relative to the catheter body 402. In some embodiments, the slider mechanism 406 can be configured to engage with at least two channels 420, 422 formed in the housing 408. The slider mechanism 406 is in the first or forward position when engaged with channel 420 (as illustrated in FIG. 23), and is in the second or rearward position when engaged with channel 422. With reference to FIG. 21, the release mechanism 410 can have one or more opposing tabs 411 that can selectively engage with the channels 420, 422. The channels 420, 422 can be formed in radially opposing positions in the housing 408. A spring member 424, which can be a cantilevered spring member, can bias each of the opposing tabs 411 supported by the release mechanism 410 in the direction defined by arrows A9 shown in FIG. 20 to selectively engage with the channels 420, 422.

As illustrated, the tabs 411 can engage with the channels 420, 422 and extend through the housing 408 so that a user can depress the release mechanism 410 against the bias of the spring member 424 by squeezing the tabs 411 together in the direction defined by arrows A10 shown in FIG. 23, so that the slider mechanism 406 and the sheath 416 can be translated axially between at least the first and second positions. Channels, protrusions, or other features, such as the protrusions 434 formed on the inside of the housing 406 can be configured to engage with or receive the slider mechanism 406 to provide increased support to the slider mechanism 406 as the slider mechanism 406 is translated relative to the catheter body 402.

In some embodiments, openings (not illustrated) can be formed in the housing 408 to allow a user to view the position of the housing 408 relative to the catheter body 402, or to view other aspects of the catheter body 402. Further, in some embodiments, the catheter system 400 can support a mandrel 440 having a handle portion 442. The mandrel 440 can be advanceable within a lumen formed in the catheter body 402, such as an inflation lumen or separate lumen configured to receive the mandrel 440. The mandrel 440 can have any of the same features or shapes of any of the other mandrels disclosed herein.

Although the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It can be also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it can be intended that the scope of the present inventions herein disclosed should not be limited by the particular disclosed embodiments described above.

What is claimed is:

1. A catheter system comprising:
   a catheter body comprising a proximal end, a distal end, and a first lumen extending axially through at least a portion of the catheter body, the first lumen being configured to receive a guidewire;
   a first opening extending laterally through the catheter body, the first opening being in communication with the first lumen and being positioned closer to the proximal end of the catheter body than the distal end of the catheter body, and wherein the first opening is configured to remain outside a body of a patient during a procedure;
   a distal portion of the catheter body extending distally of the first opening and a proximal portion of the catheter body extending proximally of the first opening, the distal portion comprising sufficient flexibility to permit the distal portion to track over the guidewire in a blood vessel to a remote location; and
   a sheath supported by the catheter body, the sheath being slidable relative to the catheter body;
   wherein:
   the sheath is movable between at least a first position and a second position;
   in the first position, the first opening is substantially covered by the sheath such that the guidewire is prevented from advancing through the first opening when the sheath is in the first position;
   in the second position, the first opening is substantially uncovered; and
   when the sheath is in the second position, the catheter system is configured to direct the guidewire being advanced through the first lumen to pass through the first opening such that a working length of the catheter system is shorter than when the sheath is in the first position;
   wherein the proximal and distal portions are non-overlapping when the sheath is in the first position and when the sheath is in the second position;
   wherein the catheter body defines an inflection point adjacent to the first opening, the inflection point being an approximate location wherein the catheter body defines a bend having an angle of curvature defined between the distal portion and a longitudinal axis of the proximal portion;
   wherein the angle of curvature is greater in a first configuration than in a second configuration, the bend of the catheter body in the first configuration comprising a first inwardly bent portion and a second outwardly bent portion that is circumferentially opposite the first inwardly bent portion, the first inwardly bent portion defining a first interior angle between the proximal catheter body portion and the distal catheter body portion, the second outwardly bent portion defining a second exterior angle between the proximal catheter body portion and the distal catheter body portion, the second exterior angle greater than the first interior angle in the first configuration, the first opening positioned along the second outwardly bent portion such that the catheter body is bent away from the first opening in the first configuration, the first opening positioned relative to the inflection point such that, in the first configuration, the guidewire can pass through the first lumen from the distal portion of the catheter body within the body of the patient, out of the first lumen through the first opening and in a proximal direction outside the body of the patient; and
   wherein the catheter body is biased so as to be relaxed in the first configuration.

2. The catheter system of claim 1, wherein the first opening extends laterally through a side wall of the catheter body.

3. The catheter system of claim 1, wherein the sheath is axially movable relative to the catheter body.

4. The catheter system of claim 1, wherein the catheter body further comprises a second lumen extending axially at least partially through the catheter body configured to communicate with an expandable balloon supported at the distal end of the catheter body.

5. The catheter system of claim 1, wherein, in the first configuration, the sheath is in the second position, and in the second configuration, the sheath is in the first position.

6. The catheter system of claim 1, wherein the angle of curvature is substantially greater in the first configuration than in the second configuration.

7. A catheter system comprising:
   a catheter body comprising a proximal end, a distal end, and a first lumen extending axially through at least a portion of the catheter body, the first lumen being configured to receive a guidewire;
   a first opening extending laterally through the catheter body, the first opening being in communication with the first lumen and being positioned closer to the proximal end of the catheter body than the distal end of the catheter body, wherein the first opening is configured to remain outside a body of a patient during a procedure;
   a proximal catheter body portion extending from the proximal end of the catheter body to the first opening; and a distal catheter body portion extending from the first opening to the distal end of the catheter body, the distal catheter body portion comprising sufficient flexibility to permit the distal catheter body portion to track over the guidewire in a blood vessel to a remote location; wherein:

the catheter body defines an inflection point adjacent to the first opening, the inflection point being an approximate location wherein the catheter body defines a bend having an angle of curvature defined between the distal catheter body portion and a longitudinal axis of the proximal catheter body portion;

the catheter body is movable between at least a first configuration and a second configuration, the bend of the catheter body in the first configuration comprising a first inwardly bent portion and a second outwardly bent portion that is circumferentially opposite the first inwardly bent portion, the first inwardly bent portion defining a first interior angle between the proximal catheter body portion and the distal catheter body portion, the second outwardly bent portion defining a second exterior angle between the proximal catheter body portion and the distal catheter body portion, the second exterior angle greater than the first interior angle in the first configuration, the first opening positioned along the second outwardly bent portion such that the catheter body is bent away from the first opening in the first configuration;

the angle of curvature is greater in the first configuration than in the second configuration, the first opening positioned relative to the inflection point such that, in the first configuration, the guidewire can pass through the first lumen from the distal catheter body portion within the body of the patient, out of the first lumen through the first opening and in a proximal direction outside the body of the patient;

the distal catheter body portion is non-overlapping in both the first and second configurations when the catheter body is in a relaxed state; and the catheter body is biased so as to be relaxed in the first configuration.

8. The catheter system of claim 7, wherein the catheter body further comprises a second lumen extending axially at least partially through the catheter body configured to communicate with an expandable balloon supported at the distal end of the catheter body.

9. The catheter system of claim 7, further comprising a mandrel that is extendable through at least a portion of the catheter body adjacent to the first opening to increase a stiffness of the catheter body adjacent to the first opening.

10. The catheter system of claim 9, wherein the mandrel extends through at least a portion of an inflation lumen of the catheter body.

11. The catheter system of claim 7, wherein the distal catheter body portion is generally straight in both the first and second configurations when the catheter body is in the relaxed state.

12. The catheter system of claim 7, wherein the angle of curvature is substantially greater in the first configuration than in the second configuration.

13. The catheter system of claim 7, wherein the angle of curvature in the first configuration is approximately 30 degrees.

14. The catheter system of claim 7, wherein the angle of curvature in the first configuration is from approximately 10 degrees to approximately 30 degrees.

15. The catheter system of claim 7, wherein the angle of curvature in the second configuration is approximately 0 degrees.

16. The catheter system of claim 7, wherein the angle of curvature in the second configuration is from approximately 0 degrees to approximately 5 degrees.

17. The catheter system of claim 7, comprising a mandrel supported within the catheter body, the mandrel configured to bias the catheter body toward the first configuration.

18. The catheter system of claim 7, wherein the catheter body is heat set in the first configuration.

19. The catheter system of claim 7, further comprising a sheath supported by the catheter body, the sheath being movable between at least a first position and a second position such that the sheath substantially covers the first opening in the first position and substantially exposes the first opening in the second position.

20. The catheter system of claim 19, wherein the catheter system is configured such that moving the sheath from the first to the second position moves the catheter body from the first to the second configuration.

21. The catheter system of claim 19, further comprising a housing supported about the proximal catheter body portion, the housing being in communication with the sheath and being configured to move the sheath between the first and second positions.

* * * * *